(12) United States Patent
Yamada et al.

(10) Patent No.: US 7,691,492 B2
(45) Date of Patent: Apr. 6, 2010

(54) FLUORENE COMPOUND AND ORGANIC LIGHT-EMITTING DEVICE USING SAME

(75) Inventors: Naoki Yamada, Inagi (JP); Akihito Saitoh, Yokohama (JP); Keiji Okinaka, Kawasaki (JP); Koichi Suzuki, Yokohama (JP); Akihiro Senoo, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 919 days.

(21) Appl. No.: 11/102,668

(22) Filed: Apr. 11, 2005

(65) Prior Publication Data

US 2005/0236977 A1 Oct. 27, 2005

(30) Foreign Application Priority Data

Apr. 12, 2004 (JP) .............................. 2004-117020
Apr. 5, 2005 (JP) .............................. 2005-108186

(51) Int. Cl.
*H01L 51/54* (2006.01)
*H01J 1/62* (2006.01)
*H01J 63/04* (2006.01)
*C07C 255/49* (2006.01)
*C07C 211/54* (2006.01)
*C07C 13/465* (2006.01)

(52) U.S. Cl. .................. 428/690; 428/917; 313/504; 313/506; 558/420; 564/426; 570/183; 585/27

(58) Field of Classification Search ................ 313/504, 313/506; 558/420; 564/426; 570/183; 585/27
See application file for complete search history.

(56) References Cited

U.S. PATENT DOCUMENTS 4,539,507 A 9/1985 Van Slyke et al. ........... 313/504

(Continued)

FOREIGN PATENT DOCUMENTS

JP 02-247278 10/1990

(Continued)

OTHER PUBLICATIONS

Answers.com, search of "adamantane", http://www.answers.com/topic/adamantane (May 28, 2009).*

(Continued)

*Primary Examiner*—Dawn Garrett
(74) *Attorney, Agent, or Firm*—Fitzpatrick, Cella, Harper & Scinto

(57) ABSTRACT

A novel substituted fluorene compound is provided which is represented by the general formula [I]:

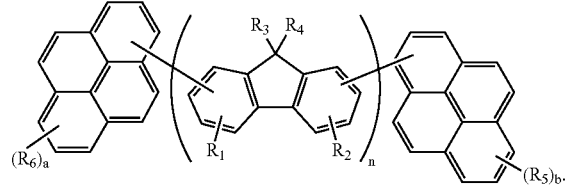

5 Claims, 4 Drawing Sheets

U.S. PATENT DOCUMENTS

| | | | |
|---|---|---|---|
| 4,720,432 A | 1/1988 | Van Slyke et al. | 428/457 |
| 4,885,211 A | 12/1989 | Tang et al. | 428/457 |
| 5,130,603 A | 7/1992 | Tokailin et al. | 313/504 |
| 5,151,629 A | 9/1992 | Van Slyke | 313/504 |
| 5,227,252 A | 7/1993 | Murayama et al. | 428/690 |
| 5,247,190 A | 9/1993 | Friend et al. | 257/40 |
| 5,317,169 A | 5/1994 | Nakano et al. | 257/40 |
| 5,382,477 A | 1/1995 | Saito et al. | 428/690 |
| 5,409,783 A | 4/1995 | Tang et al. | 428/690 |
| 5,514,878 A | 5/1996 | Holmes et al. | 257/40 |
| 5,672,678 A | 9/1997 | Holmes et al. | 528/373 |
| 6,652,997 B2 | 11/2003 | Suzuki et al. | 428/690 |
| 6,916,555 B2 | 7/2005 | Suzuki et al. | 428/690 |
| 6,921,588 B2 * | 7/2005 | Toguchi et al. | 428/690 |
| 7,241,513 B2 * | 7/2007 | Suzuki et al. | 428/690 |
| 7,491,450 B2 * | 2/2009 | Okinaka et al. | 428/690 |
| 2004/0253389 A1 | 12/2004 | Suzuki et al. | 428/1.1 |
| 2004/0263067 A1 | 12/2004 | Saitoh et al. | 313/504 |
| 2004/0265632 A1 | 12/2004 | Okinaka et al. | 428/690 |
| 2005/0099115 A1 | 5/2005 | Saitoh et al. | 313/504 |
| 2005/0106414 A1 | 5/2005 | Saitoh et al. | 428/690 |

FOREIGN PATENT DOCUMENTS

| | | | |
|---|---|---|---|
| JP | 03-255190 | | 11/1991 |
| JP | 04-145192 | | 5/1992 |
| JP | 05-202356 | | 8/1993 |
| JP | 05-247460 | | 9/1993 |
| JP | 09-202878 | | 8/1997 |
| JP | 09-227576 | | 9/1997 |
| WO | WO 2004/020372 | * | 3/2004 |

OTHER PUBLICATIONS

Yamamoto, et al; "A Novel Type of Polycondensation Utilizing Transition Metal-Catalyzed C-C Coupling"; Bulletin of The Chemical Society of Japan; vol. 51; No. 7; pp. 2091-2097 (1978).

Ghosal, et al; "Formation of 1,3-Dienes, and Biphenyls via the copper (II) Nitrate Mediated Coupling of Organotin compounds"; J. Org. Chem., vol. 52, No. 19, pp. 4296-4298 (1987).

Burroughes, et al; Light-emitting diodes based on conjugated polymers; Nature, vol. 347, pp. 539-541 (1990).

Miyaura, et al; "Palladium-Catalyzed Cross-Coupling Reactions of Organoboron Compounds"; Chem. Rev., vol. 95, No. 7, pp. 2457-2483 (1995).

Baldo, et al; "Highly Efficient phosphorescent emission from organic electroluminescent devices"; Nature, vol. 395, pp. 151-154 (1998).

* cited by examiner

FLUORENE COMPOUND AND ORGANIC LIGHT-EMITTING DEVICE USING SAME

BACKGROUND OF THE INVENTION

1. Field of the Invention

The present invention relates to a novel organic compound and an organic light-emitting device using the same.

2. Related Background Art

An organic light-emitting device is a device in which a thin film comprising a fluorescent organic compound or a phosphorescent organic compound is sandwiched between an anode and a cathode and electrons and holes are injected from the respective electrodes to generate excitons of the fluorescent compound or the phosphorescent compound, whereby light emitted when the excitons return to a ground state is utilized.

According to a study at Kodak company in 1987 (Appl. Phys. Lett. 51, 913 (1987)), there has been reported a light emission of approximately 1000 cd/m$^2$ at an applied voltage of approximately 10 V in a device having a function-separation type two-layer structure using ITO as an anode, a magnesium-silver alloy as a cathode, an aluminum quinolinol complex as an electron-transporting material and a light-emitting material, and a triphenylamine derivative as a hole-transporting material. Related patents include U.S. Pat. Nos. 4,539,507, 4,720,432, and 4,885,211.

In addition, emission of a light within the range of from ultraviolet to infrared light can be generated by changing the type of fluorescent organic compound. In recent years extensive studies have been made on various kinds of compounds. For instance, such compounds are disclosed in U.S. Pat. Nos. 5,151,629, 5,409,783 and 5,382,477, and Japanese Patent Application Laid-Open Nos. H2-247278, H3-255190, H5-202356, H9-202878 and H9-227576.

In recent years, many studies have been made into the application of energy in a triplet state to EL by using a phosphorescent compound as a light-emitting material. A high emission efficiency exhibited by an organic light-emitting device using an iridium complex as a light-emitting material has been reported by a group at Princeton University (Nature 395, 151 (1998)).

Furthermore, in addition to the organic light-emitting device using a low molecular weight material as mentioned above, an organic light-emitting device using a conjugated polymer has been reported by a group at Cambridge University (Nature, 347, 539 (1990)). In this report, light emission from a single layer was confirmed using a film of polyphenylenevinylene (PPV) formed by application. Related patents to an organic light-emitting device using a conjugated polymer include U.S. Pat. Nos. 5,247,190, 5,514,878, 5,672,678, and Japanese Patent Application Laid-Open Nos. H4-145192 and H5-247460.

The recent progress in organic light-emitting devices is remarkable as described above and the characteristics of such devices enable a light-emitting device with a high luminance even at a low applied voltage, a wide range of emission wavelengths, a high-speed response, a small thickness and a light weight, thus suggesting the possibility of application to a variety of uses.

However, the present situation calls for optical output with even higher luminance or higher conversion efficiency. In addition, many problems still remain to be solved regarding durability against the change over time due to long-term use, deterioration caused by atmospheric gas containing oxygen, moisture, or the like. Furthermore, when considering application to a full color display or similar device, the present art is still insufficient against problems relating to the needs for light emission of blue, green, and red with a high color purity.

SUMMARY OF THE INVENTION

It is, therefore, an object of the present invention to provide a novel substituted fluorene compound.

It is another object of the present invention to provide an organic light-emitting device using a substituted fluorene compound and having an optical output with an extremely high efficiency and a high luminance.

It is still another object of the present invention to provide an organic light-emitting device having an extremely high durability.

It is yet another object of the present invention to provide an organic light-emitting device that can easily be produced at a relatively low cost.

Namely, the fluorene compound according to the present invention is represented by the general formula [I]:

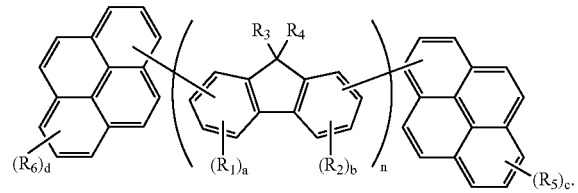

wherein the two pyrenyl groups are each independently bonded at position 1 or 4 thereof to the fluorenyl group;

each $R_1$ and $R_2$, independently, is a hydrogen atom, a substituted or unsubstituted alkyl group, a substituted or unsubstituted aralkyl group, a substituted or unsubstituted aryl group, a substituted or unsubstituted heterocyclic group, a substituted amino group, cyano group, or a halogen atom;

each $R_3$ and $R_4$, independently, is a hydrogen atom, a substituted or unsubstituted alkyl group, a substituted or unsubstituted aralkyl group, a substituted or unsubstituted aryl group, or a substituted or unsubstituted heterocyclic group;

each $R_5$ and $R_6$, independently, is substituted or unsubstituted isopropyl group, sec-butyl group, tert-butyl group, 1-adamantyl group, 2-adamantyl group, isoamyl group, trimethylsilyl group or triphenylsilyl group;

a and b are independently an integer of 0 to 9;

c and d are independently an integer of 1 to 9; and n is an integer of 1 to 10.

That is, in the above general formula [I], $R_1(s)$ and $R_2(s)$ which are bonded to different fluorene rings may be the same or different, and $R_1(s)$ and $R_2(s)$ which are bonded to the same fluorene ring may be the same or different. Further, a and b may be the same or different, and when a and b are each an integer of 2 or more, $R_1$s and $R_2$s may be the same or different. Moreover, $R_3(s)$ and $R_4(s)$ which are bonded to different fluorene rings may be the same or different, and $R_3$ and $R_4$ which are bonded to the same fluorene ring may be the same or different. In addition, $R_5(s)$ and $R_6(s)$ may be the same or different; c and d may be the same or different; and when c and d are each an integer of 2 or more, $R_5$s and $R_6$s may be the same or different.

Further, the organic light-emitting device according to the present invention comprises a pair of electrodes including an anode and a cathode, and at least one layer comprising an organic compound sandwiched between the pair of electrodes, wherein at least one of the at least one layer comprising the organic compound contains at least one of the above-described fluorene compounds.

An organic light-emitting device which uses the fluorene compound represented by the general formula [I] can emit light at a high luminance with a low applied voltage and has excellent durability. In particular, an organic layer that contains the fluorene compound according to the present invention is excellent as an electron-transporting layer and as a light-emitting layer.

In addition, the device can be prepared by using a vacuum evaporation method or a casting method, so that a device having a large area can easily be prepared at a relatively low cost.

DESCRIPTION OF THE PREFERRED EMBODIMENTS

Figure 1:
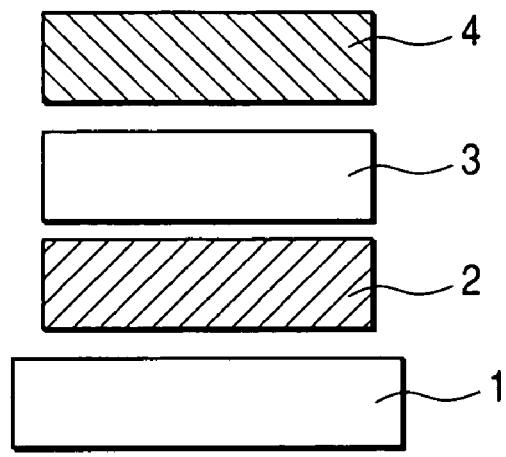
FIG. 1 is a cross-sectional view showing an example of the organic light-emitting device in accordance with the present invention.

The present invention will now be described in detail.

First, the fluorene compound of the present invention will be described.

The fluorene compound of the present invention is represented by the above general formula [I].

Specific examples of the substituents in the above general formula [I] will be shown below.

Examples of the alkyl group include methyl group, ethyl group, n-propyl group, isopropyl group, n-butyl group, tert-butyl group, sec-butyl group, octyl group, 1-adamantyl group, 2-adamantyl group and the like.

Examples of the aralkyl group include benzyl group, phenethyl group and the like.

Examples of the aryl group include phenyl group, biphenyl group, terphenyl group and the like.

Examples of the heterocyclic group include thienyl group, pyrrolyl group, pyridyl group, oxazolyl group, oxadiazolyl group, thiazolyl group, thiadiazolyl group, terthienyl group and the like.

Examples of the substituted amino group include dimethylamino group, diethylamino group, dibenzylamino group, diphenylamino group, ditolylamino group, dianisoylamino group and the like.

Examples of the halogen atom include fluorine, chlorine, bromine, iodine and the like. Examples of the hydrogen atom include a radioisotope such as deuterium.

Examples of the substituents which the above-mentioned substituents may have include an alkyl group such as methyl group, ethyl group, and propyl group; an aralkyl group such as benzyl group and phenethyl group; an aryl group such as phenyl-group and biphenyl group; a heterocyclic group such as thienyl group, pyrrolyl group, and pyridyl group; amino groups such as dimethylamino group, diethylamino group, dibenzylamino group, diphenylamino group, ditolylamino group, and dianisoylamino group; an alkoxyl group such as methoxyl group, ethoxyl group, propoxyl group, and phenoxyl group; cyano group; a halogen atom such as fluorine, chlorine, bromine, and iodine; and the like.

Next, typical examples of the fluorene compound of the present invention will be given. However, the present invention is not limited thereto.

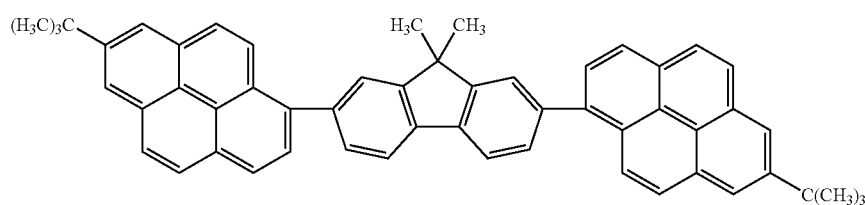

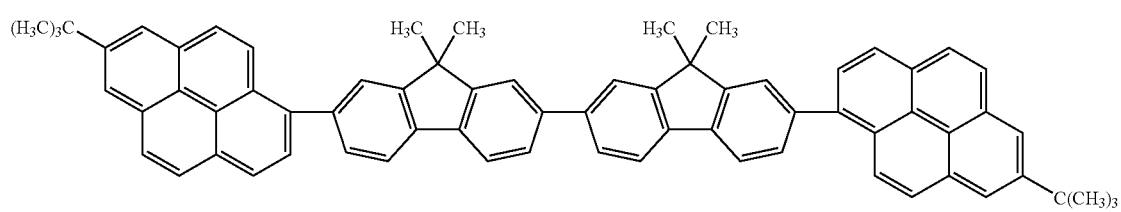

-continued
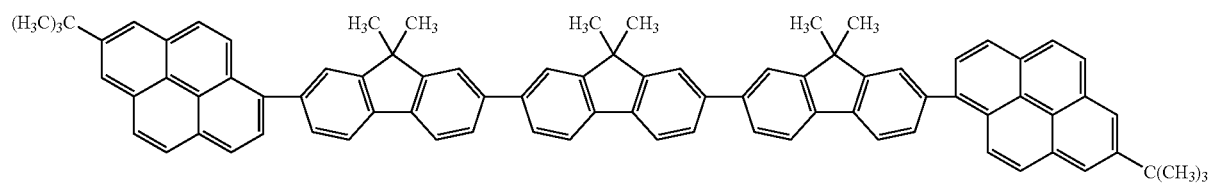
3
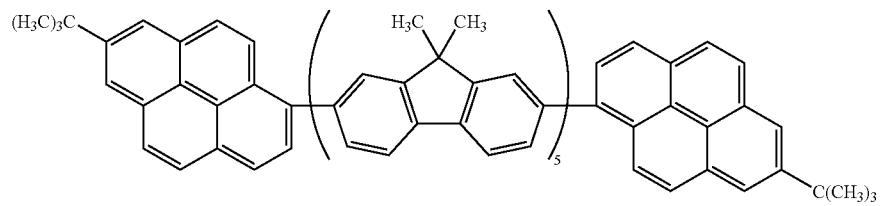
4
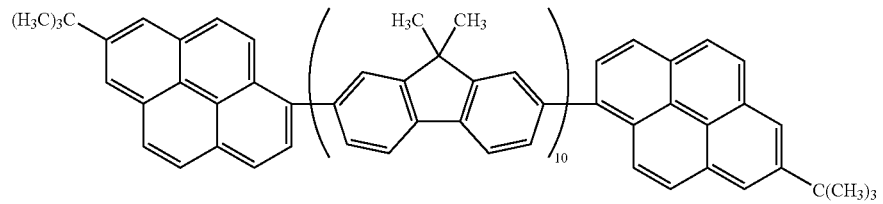
5
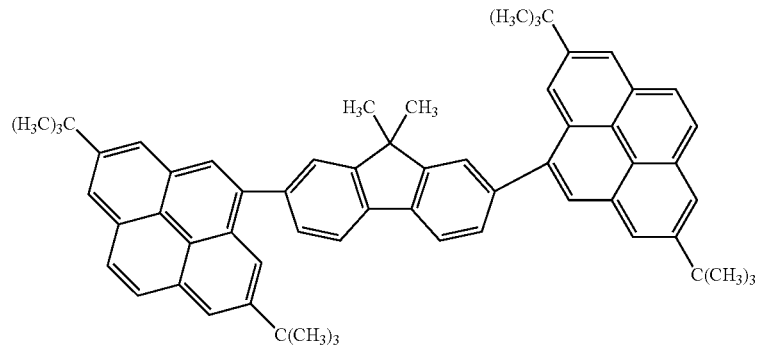
6
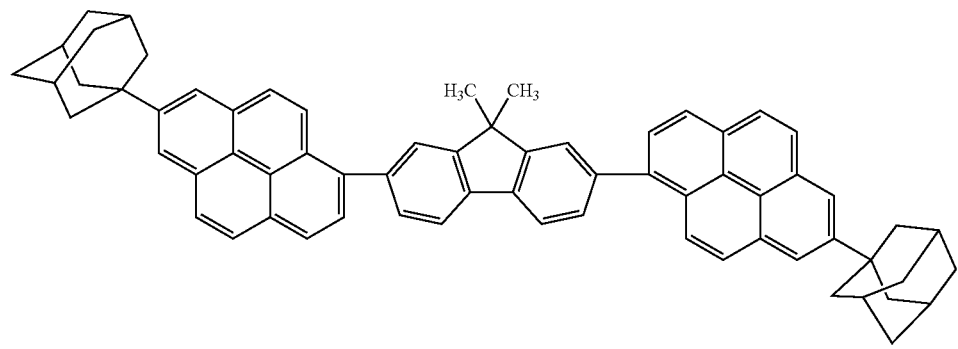
7

8
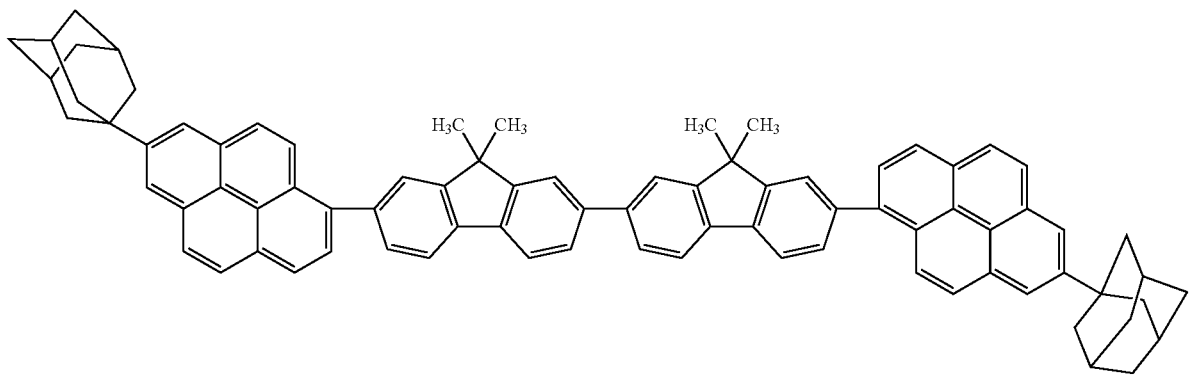
9
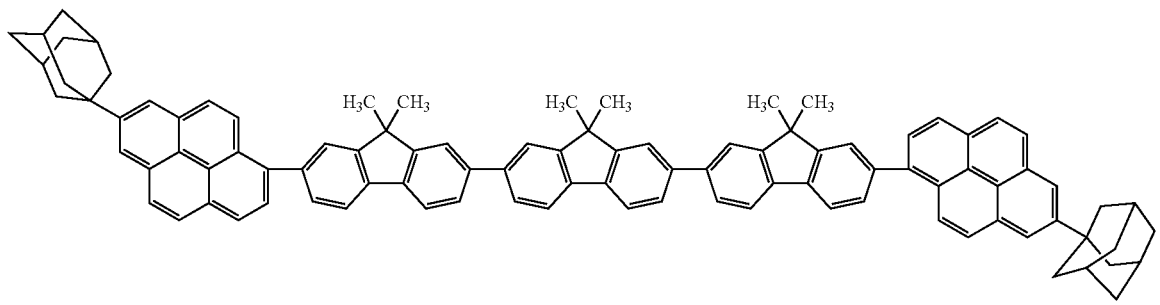
10
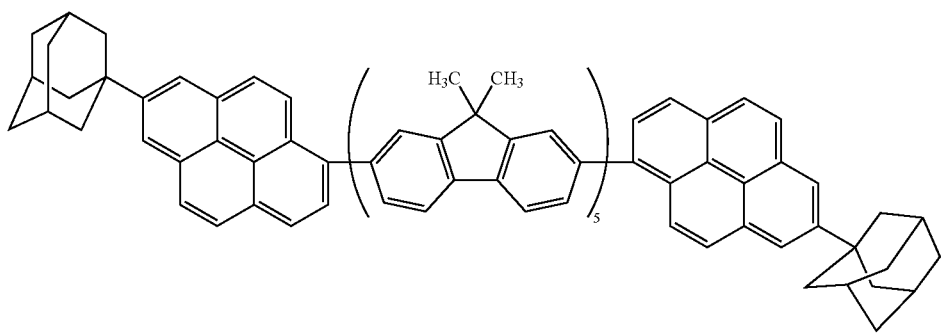
11
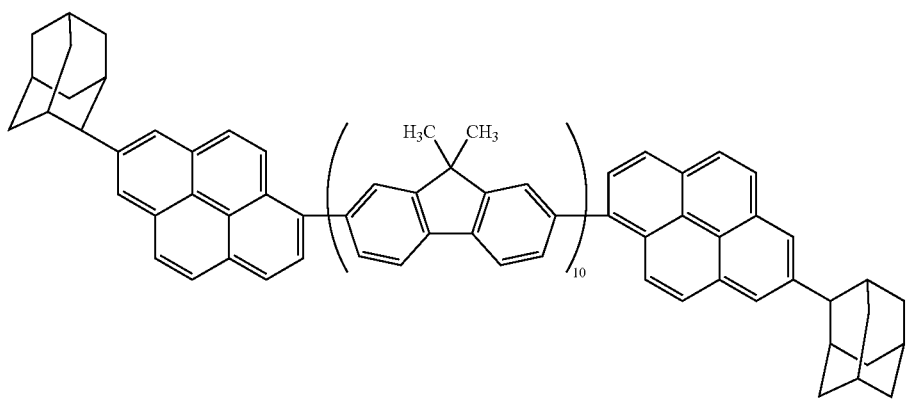

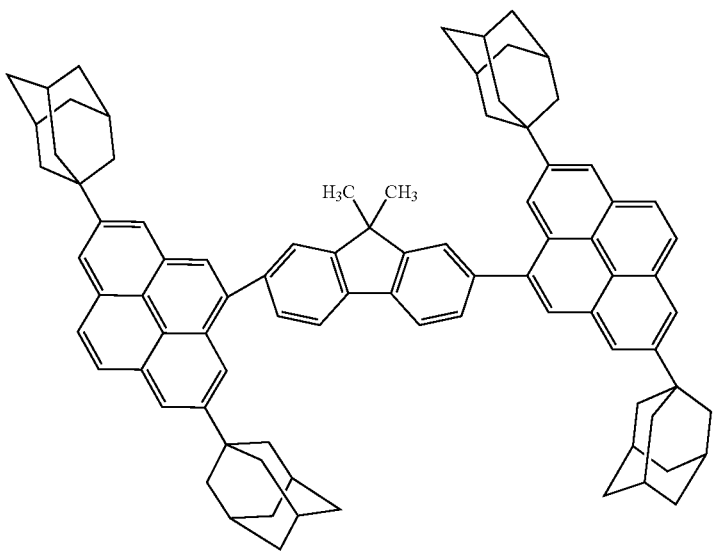

-continued
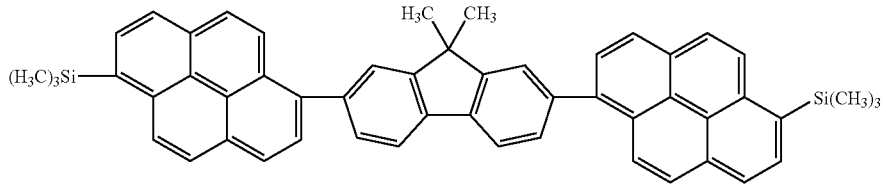
16
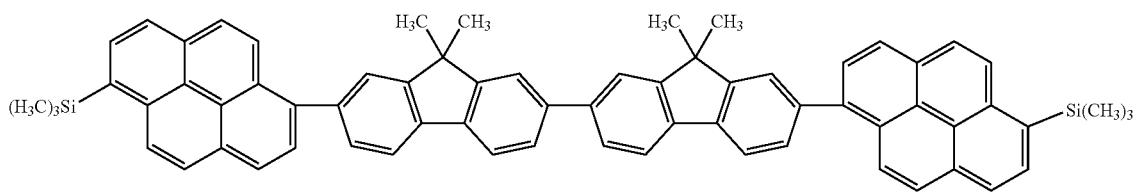
17
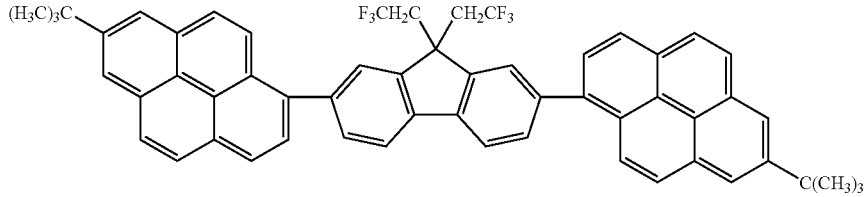
18
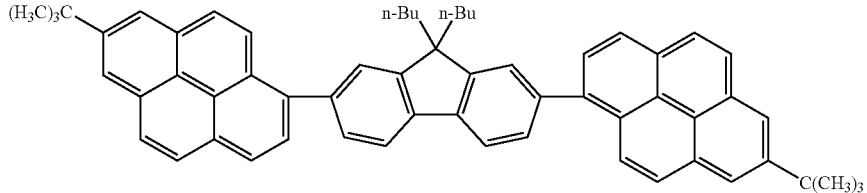
19
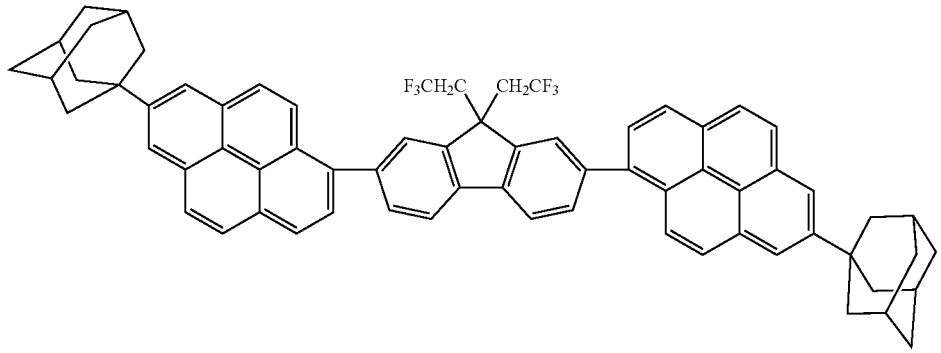
20
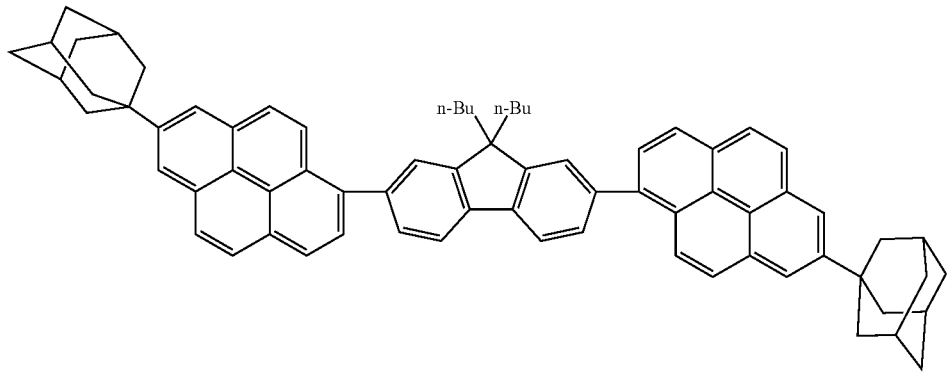
21

-continued
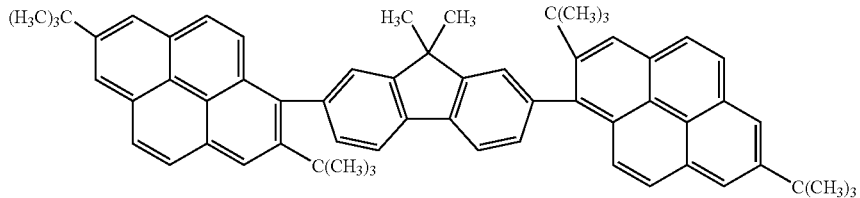
22
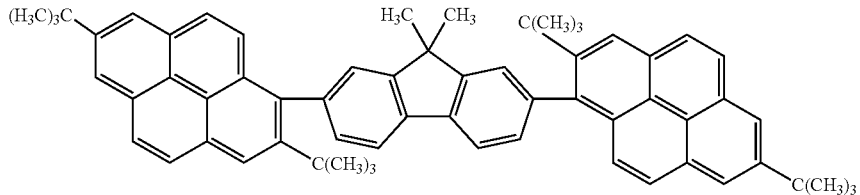
30
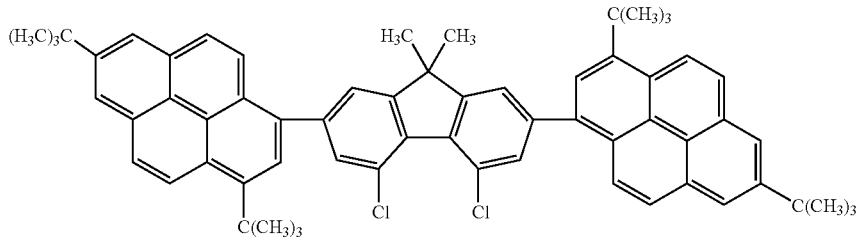
31
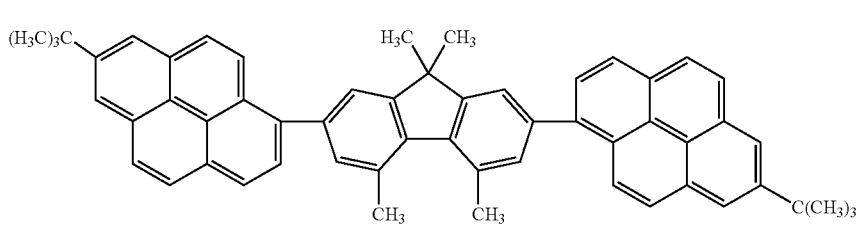
32
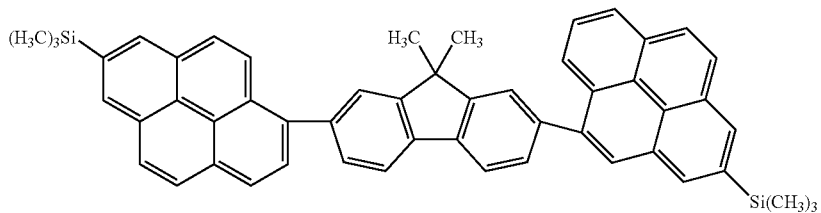
33
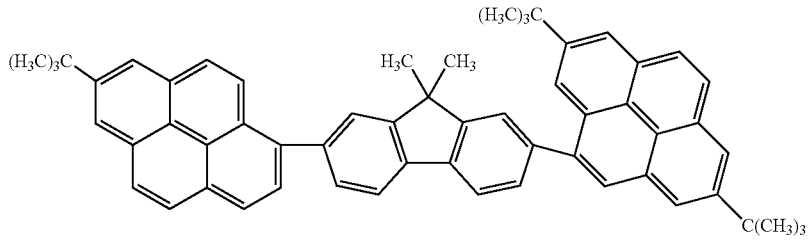
34

Particularly preferable ones of these are the following compounds.

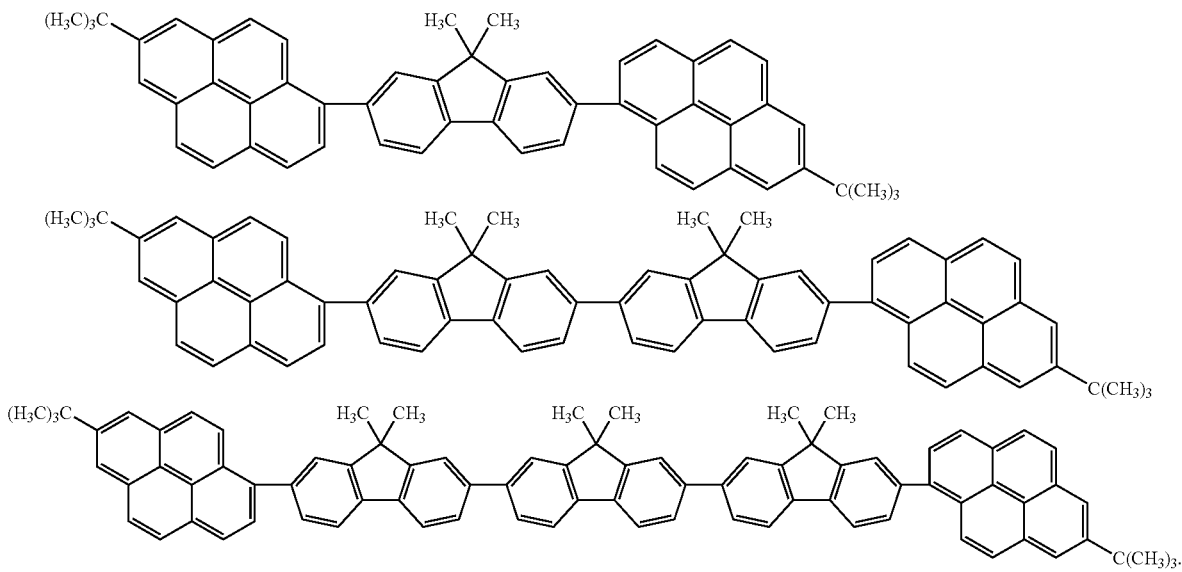

The fluorene compound of the present invention is superior to the conventional compounds in electron-transporting properties, light mission properties and durability, which is useful for a layer containing an organic compound of an organic light-emitting device, in particular for an electron-transporting layer and a light-emitting layer. In addition, a layer formed by a vacuum evaporation method, a solution application method, etc., does not readily undergo crystallization or the like and is excellent in stability over time.

Furthermore, because substituted or unsubstituted isopropyl group, sec-butyl group, tert-butyl group, 1-adamantyl group, 2-adamantyl group, isoamyl group, trimethylsilyl group or triphenylsilyl group is incorporated into the pyrene ring, molecular association can be suppressed, lowering in emission efficiency or the like due to concentration quenching can be restrained, and solubility increases to enable an organic layer to be readily formed by a solution application method.

The fluorene compound of the present invention can be synthesized by a well-known method and obtained by using, for example, a synthesis method such as the Suzuki coupling method (e.g., Chem. Rev. 1995, 95, 2457-2483) using a palladium catalyst, the Yamamoto method (e.g., Bull. Chem. Soc. Jpn. 51, 2091, 1978) using a nickel catalyst, or a method in which synthesis is performed by using an aryl tin compound (e.g., J. Org. Chem., 52, 4296, 1987), or by alkylation using a Friedel-Crafts reaction.

Next, the organic light-emitting device of the present invention will be described in detail below.

The organic light-emitting device of the present invention comprises a pair of electrodes including an anode and a cathode, and at least one layer comprising an organic compound sandwiched between the pair of electrodes, wherein at least one of the at least one layer comprising the organic compound contains at least one of the fluorene compounds represented by the above general formula [I].

In the organic light-emitting device of the present invention, it is preferable that at least an electron-transporting layer or a light-emitting layer of the layer(s) comprising an organic compound comprises at least one of the above-mentioned fluorene compounds.

In the organic light-emitting device of the present invention, the fluorene compound represented by the above general formula [I] is formed between the anode and the cathode by a vacuum evaporation method or a solution application method. The organic layer is preferably formed into a thin film with a thickness of 10 μm or less, more preferably 0.5 μm or less, and most preferably 0.01 to 0.5 μm.

Further, according to a preferred embodiment of the organic light-emitting device of the present invention, at least a light-emitting layer of the layer(s) comprising the organic compound comprises at least one of the fluorene compounds represented by the above general formula [I] and either one of the arylamine compounds represented by the following general formulae [II] to [VII] or an acetylene compound represented by the following general formula [VIII].

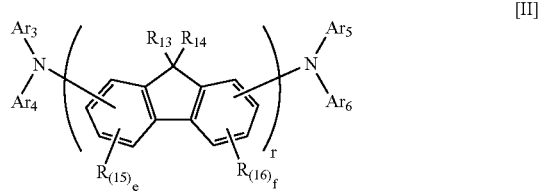

In the general formula [II], each $R_{13}$ and $R_{14}$, independently, is a hydrogen atom, a substituted or unsubstituted alkyl group, a substituted or unsubstituted aralkyl group, a substituted or unsubstituted aryl group, or a substituted or unsubstituted heterocyclic group;

each $R_{15}$ and $R_{16}$, independently, is a hydrogen atom, a substituted or unsubstituted alkyl group, a substituted or unsubstituted aralkyl group, a substituted or unsubstituted aryl group, a substituted or unsubstituted heterocyclic group, cyano group, or a halogen atom;

e and f are each independently an integer of 1 to 3;

$Ar_3$, $Ar_4$, $Ar_5$, and $Ar_6$ are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_3$ and $Ar_4$, and $Ar_5$ and $Ar_6$ can respectively be joined to form a ring; and r is an integer of 1 to 10.

That is, in the above general formula [II], $R_{13}(s)$ and $R_{14}(s)$ which are bonded to different fluorene rings may be the same or different, and $R_{13}$ and $R_{14}$ which are bonded to the same fluorene ring may be the same or different. Further, $R_{15}(s)$ and $R_{16}(s)$ which are bonded to different fluorene rings may be the same or different, and $R_{15}(s)$ and $R_{16}(s)$ which are bonded to the same fluorene ring may be the same or different. Moreover, e and f may be the same or different, and when e and f are each an integer of 2 or more, $R_{15}$s and $R_{16}$s may be the same or different. In addition, $Ar_3$, $Ar_4$, $Ar_5$, and $Ar_6$ may be the same or different.

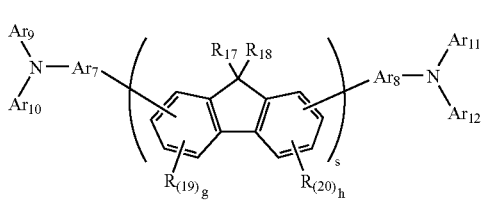

[III]

In the general formula [III], each $R_{17}$ and $R_{18}$, independently, is a hydrogen atom, a substituted or unsubstituted alkyl group, a substituted or unsubstituted aralkyl group, a substituted or unsubstituted aryl group, or a substituted or unsubstituted heterocyclic group;

each $R_{19}$ and $R_{20}$, independently, is a hydrogen atom, a substituted or unsubstituted alkyl group, a substituted or unsubstituted aralkyl group, a substituted or unsubstituted aryl group, a substituted or unsubstituted heterocyclic group, cyano group, or a halogen atom;

g and h are each independently an integer of 1 to 3;

$Ar_7$ and $Ar_8$ are each independently a substituted or unsubstituted divalent aromatic group or heterocyclic group;

$Ar_9$, $Ar_{10}$, $Ar_{11}$, and $Ar_{12}$, are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_9$ and $Ar_{10}$, and $Ar_{11}$ and $Ar_{12}$ can respectively be joined to form a ring; and s is an integer of 1 to 10.

That is, in the above general formula [III], $R_{17}(s)$ and $R_{18}(s)$ which are bonded to different fluorene rings may be the same or different, and $R_{17}$ and $R_{18}$ which are bonded to the same fluorene ring may be the same or different. Further, $R_{19}(s)$ and $R_{20}(s)$ which are bonded to different fluorene rings may be the same or different, and $R_{19}(s)$ and $R_{20}(s)$ which are bonded to the same fluorene ring may be the same or different. Moreover, g and h may be the same or different, and when g and h are each an integer of 2 or more, $R_{19}$s and $R_{20}$s may be the same or different. In addition, $Ar_7$ and $Ar_8$ may be the same or different, and $Ar_9$, $Ar_{10}$, $Ar_{11}$, and $Ar_{12}$ may be the same or different.

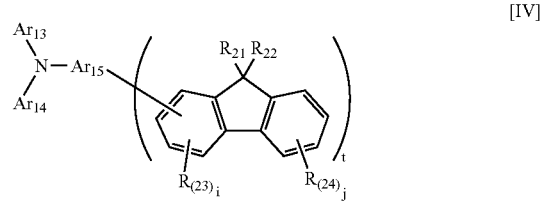

[IV]

In the general formula [IV], each $R_{21}$ and $R_{22}$, independently, is a hydrogen atom, a substituted or unsubstituted alkyl group, a substituted or unsubstituted aralkyl group, a substituted or unsubstituted aryl group, or a substituted or unsubstituted heterocyclic group;

each $R_{23}$ and $R_{24}$, independently, is a hydrogen atom, a substituted or unsubstituted alkyl group, a substituted or unsubstituted aralkyl group, a substituted or unsubstituted aryl group, a substituted or unsubstituted heterocyclic group, cyano group, or a halogen atom;

i and j are each independently an integer of 1 to 4;

$Ar_{13}$ and $Ar_{14}$ are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_{13}$ and $Ar_{14}$ can be joined to form a ring;

$Ar_{15}$ is a substituted or unsubstituted divalent aromatic group or heterocyclic group; and t is an integer of 1 to 10.

That is, in the above general formula [IV], $R_{21}(s)$ and $R_{22}(s)$ which are bonded to different fluorene rings may be the same or different, and $R_{21}$ and $R_{22}$ which are bonded to the same fluorene ring may be the same or different. Further, $R_{23}(s)$ and $R_{24}(s)$ which are bonded to different fluorene rings may be the same or different, and $R_{23}(s)$ and $R_{24}(s)$ which are bonded to the same fluorene ring may be the same or different. Moreover, i and j may be the same or different, and when i and j are each an integer of 2 or more, $R_{23}$s and $R_{24}$s may be the same or different. In addition, $Ar_{13}$ and $Ar_{14}$ may be the same or different.

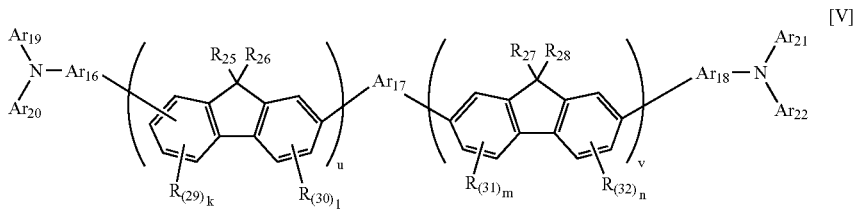

In the general formula [V], each $R_{25}$, $R_{26}$, $R_{27}$, and $R_{28}$, independently, is a hydrogen atom, a substituted or unsubstituted alkyl group, a substituted or unsubstituted aralkyl group, a substituted or unsubstituted aryl group, or a substituted or unsubstituted heterocyclic group;

each $R_{29}$, $R_{30}$, $R_{31}$, and $R_{32}$, independently, is a hydrogen atom, a substituted or unsubstituted alkyl group, a substituted or unsubstituted aralkyl group, a substituted or unsubstituted aryl group, a substituted or unsubstituted heterocyclic group, cyano group, or a halogen atom;

k, l, m, and n are each independently an integer of 1 to 3;

$Ar_{16}$, $Ar_{17}$ and $Ar_{18}$ are each independently a substituted or unsubstituted divalent aromatic group or heterocyclic group, or $Ar_{16}$ and $Ar_{18}$ are each independently a bond;

$Ar_{19}$, $Ar_{20}$, $Ar_{21}$, and $Ar_{22}$ are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_{19}$ and $Ar_{20}$, and $Ar_{21}$ and $Ar_{22}$ can respectively be joined to form a ring; and u and v are each independently an integer of 1 to 10.

That is, in the above general formula [V], $R_{25}(s)$, $R_{26}(s)$, $R_{27}(s)$, and $R_{28}(s)$ which are bonded to different fluorene rings may be the same or different, and $R_{25}$ and $R_{26}$, and $R_{27}$ and $R_{28}$ which are bonded to the same fluorene ring may respectively be the same or different. Further, $R_{29}(s)$, $R_{30}(s)$, $R_{31}(s)$, and $R_{32}(s)$ which are bonded to different fluorene rings may be the same or different, and $R_{29}(s)$ and $R_{30}(s)$, and $R_{31}(s)$ and $R_{32}(s)$ which are bonded to the same fluorene ring may respectively be the same or different. Moreover, k, l, m, and n may be the same or different, and when k, l, m, and n are each an integer of 2 or more, $R_{29}s$, $R_{30}s$, $R_{31}s$, and $R_{32}s$ may be the same or different. In addition, $Ar_{19}$, $Ar_{20}$, $Ar_{21}$, and $Ar_{22}$ may be the same or different. Furthermore, u and v may be the same or different.

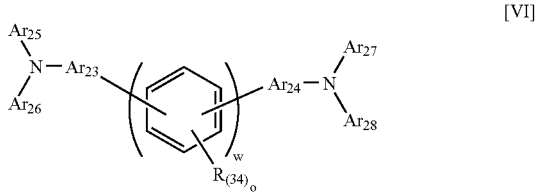

In the general formula [VI], each $R_{34}$, independently, is a hydrogen atom, a substituted or unsubstituted alkyl group, a substituted or unsubstituted aralkyl group, a substituted or unsubstituted aryl group, a substituted or unsubstituted heterocyclic group, cyano group, or a halogen atom;

o is an integer of 1 to 4;

$Ar_{23}$ and $Ar_{24}$ are each independently a substituted or unsubstituted divalent aromatic group or heterocyclic group;

$Ar_{25}$, $Ar_{26}$, $Ar_{27}$, and $Ar_{28}$ are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_{25}$ and $Ar_{26}$, and $Ar_{27}$ and $Ar_{28}$ can respectively be joined to form a ring; and w is an integer of 1 to 10.

That is, in the above general formula [VI], $R_{34}s$ which are bonded to different benzene rings may be the same or different. Further, when o is an integer of 2 or more, $R_{34}s$ may be the same or different. In addition, $Ar_{23}$ and $Ar_{24}$ may be the same or different, and $Ar_{25}$, $Ar_{26}$, $Ar_{27}$, and $Ar_{28}$ may be the same or different.

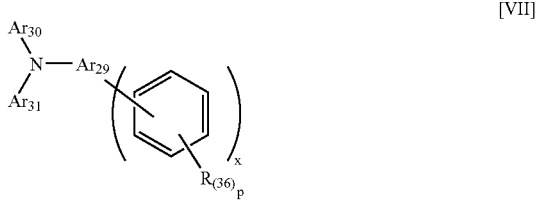

In the general formula [VII], each $R_{36}$, independently, is a hydrogen atom, a substituted or unsubstituted alkyl group, a substituted or unsubstituted aralkyl group, a substituted or unsubstituted alkoxyl group, a substituted or unsubstituted aryl group, a substituted or unsubstituted heterocyclic group, cyano group, or a halogen atom;

p is an integer of 1 to 4;

$Ar_{29}$ is a substituted or unsubstituted divalent aromatic group or heterocyclic group;

$Ar_{30}$ and $Ar_{31}$ are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_{30}$ and $Ar_{31}$ can be joined to form a ring; and x is an integer of 1 to 10.

That is, in the above general formula [VII], $R_{36}s$ which are bonded to different benzene may be the same or different. Further, when p is an integer of 2 or more, $R_{36}$ may be the same or different. In addition, $Ar_{30}$ and $Ar_{31}$ may be the same or different.

$$Ar_{32}-(C=C)_y-Ar_{33} \quad [VIII]$$

In the general formula [VIII], $A_{32}$ and $Ar_{33}$ are each independently a substituted or unsubstituted aromatic group, a substituted or unsubstituted heterocyclic group, a substituted or unsubstituted fused polycyclic aromatic group, or a substituted or unsubstituted fused heteropolycyclic group; and y is an integer of 1 to 5.

That is, in the above general formula [VIII], $Ar_{32}$ and $Ar_{33}$ may be the same or different.

Here, specific examples of the substituents in the general formulae [II] to [XIII] will be given below. Further examples of the substituents are the same as those described above for the general formula [I].

Examples of the alkoxyl group include methoxy group, ethoxy group, tert-butoxy group, n-butyl group, isopropoxy group and the like.

Examples of the fused polycyclic aromatic group include fluorenyl group, naphthyl group, fluoranthenyl group, anthryl group, phenanthryl group, pyrenyl group, tetracenyl group, pentacenyl group, triphenylenyl group, perylenyl group and the like.

Examples of the fused heteropolycyclic group include carbazolyl group, acridinyl group, phenanthrolyl group and the like.

Typical examples of the arylamine compounds represented by the general formulae [II] to [VII] and the acetylene compound represented by the general formula [VIII] will be given below, but the present invention is not limited thereto.

<General Formula [II]>

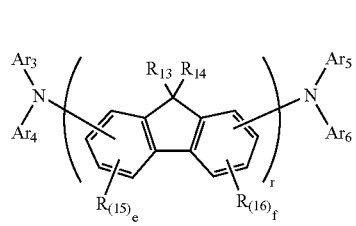

<Examples of Arylamine Compounds of General Formula [II]>

AA-1

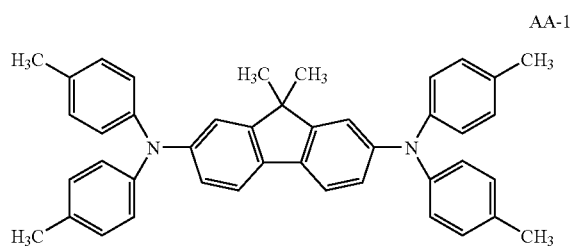

AA-2

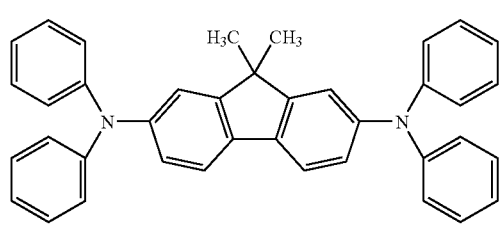

-continued

AA-3

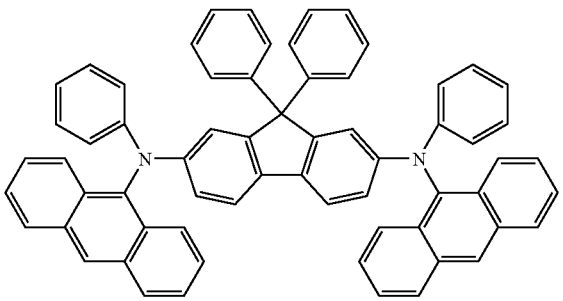

AA-4

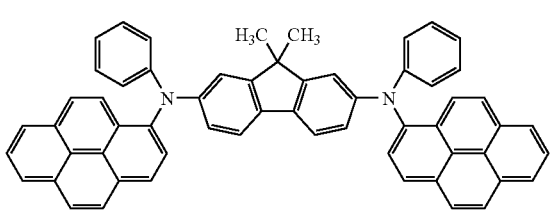

AA-5

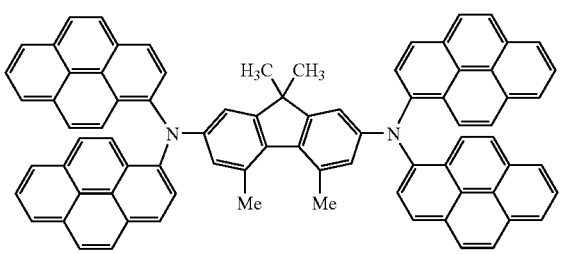

AA-6

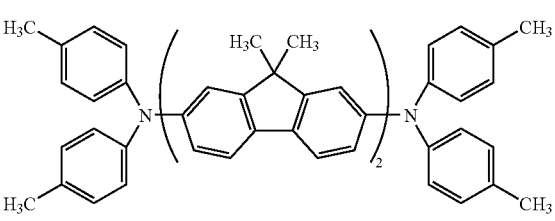

AA-7

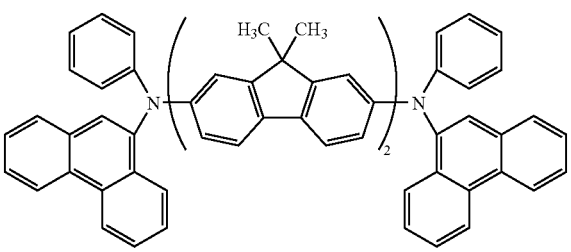

AA-8

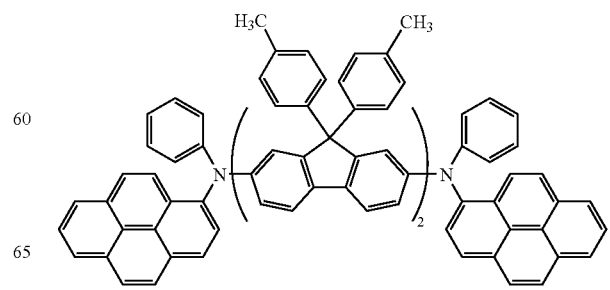

-continued
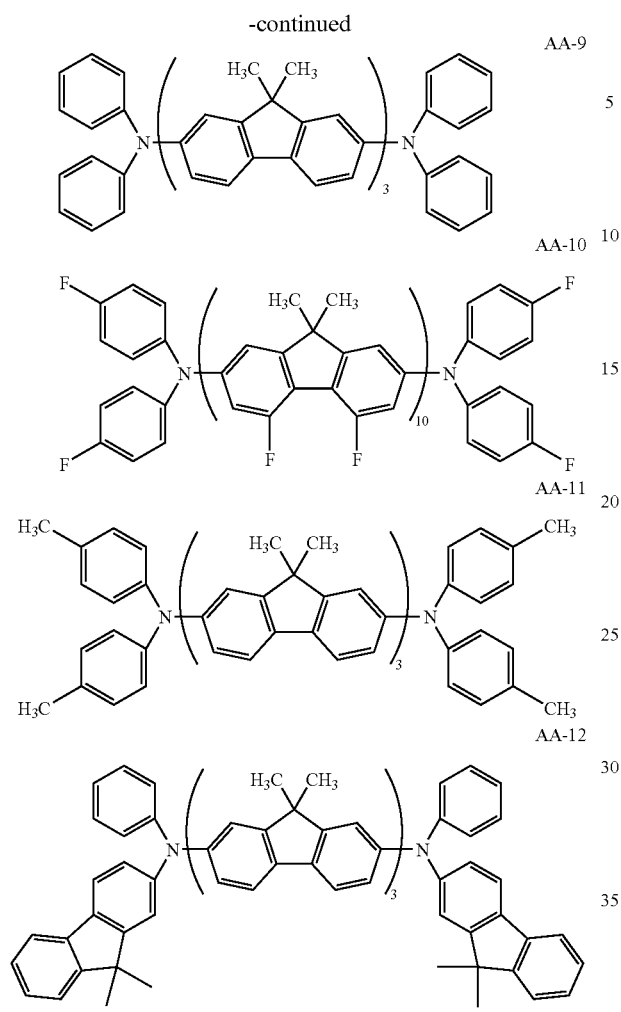
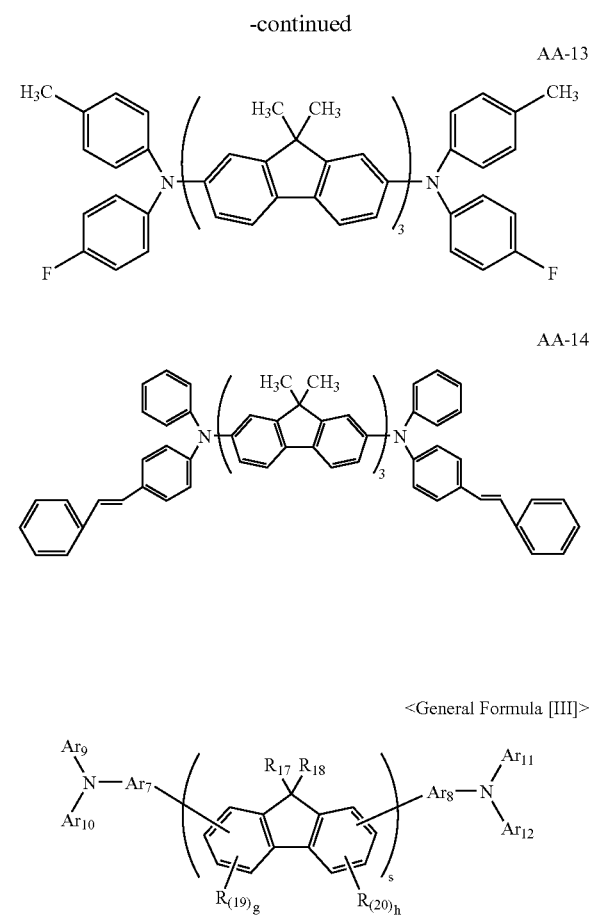
<Examples of Arylamine Compounds of General Formula [III]>
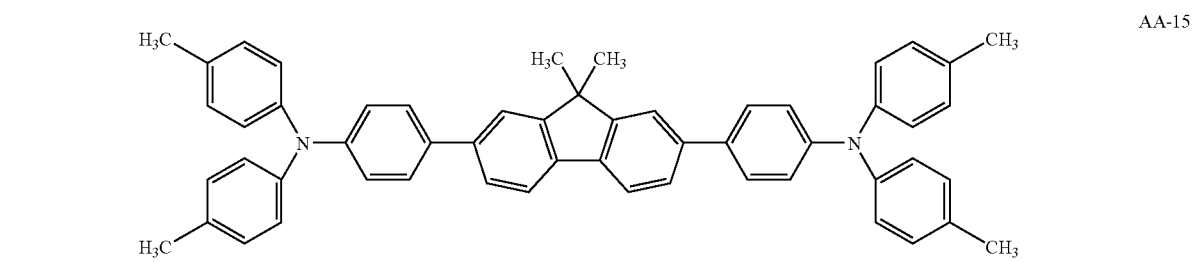
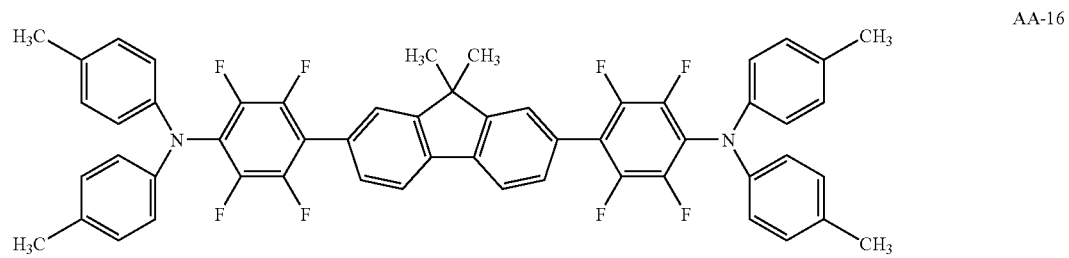

-continued
AA-17
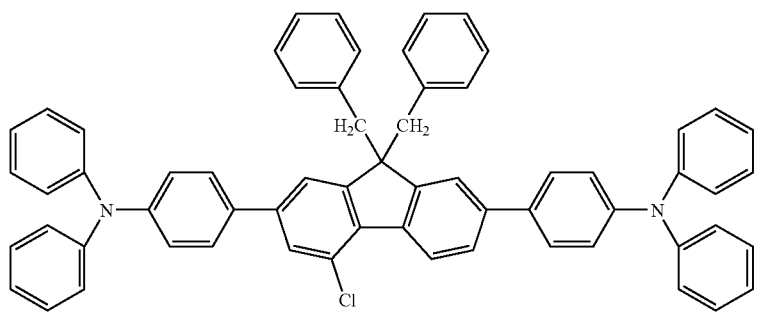
AA-18
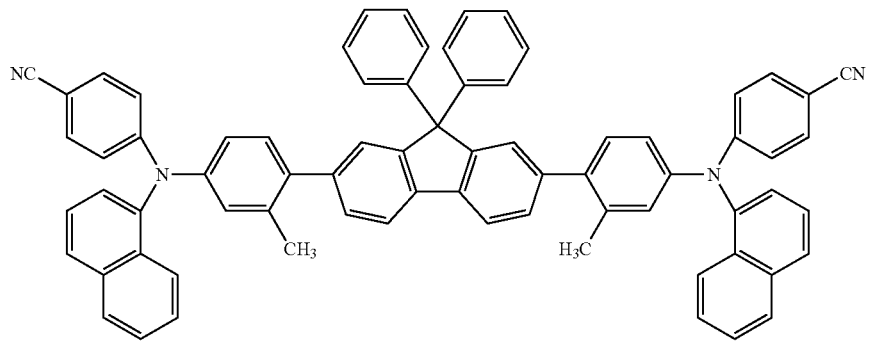
AA-19
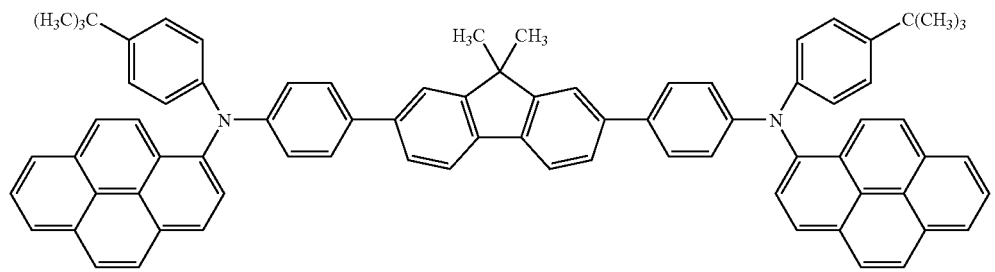
AA-20
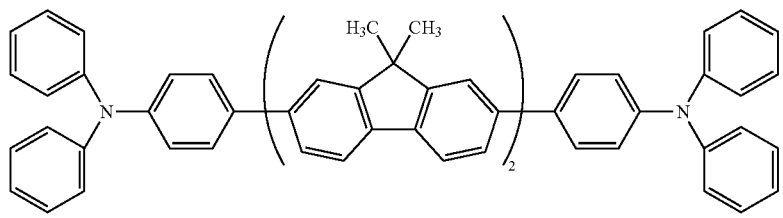
AA-21
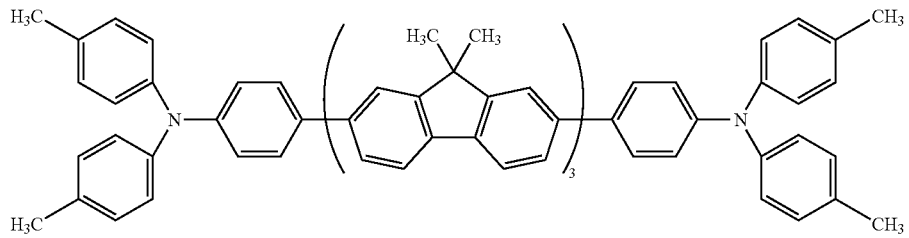
AA-22
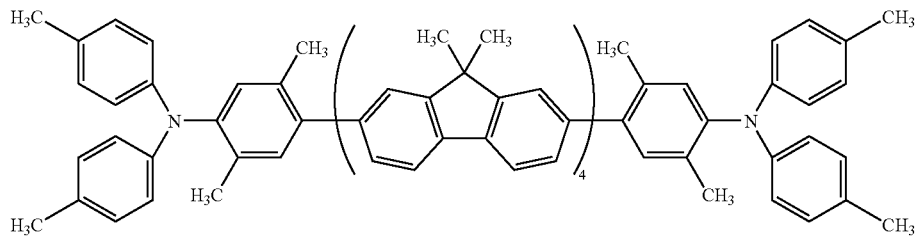

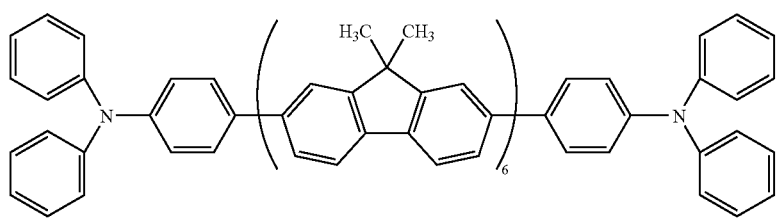
AA-23
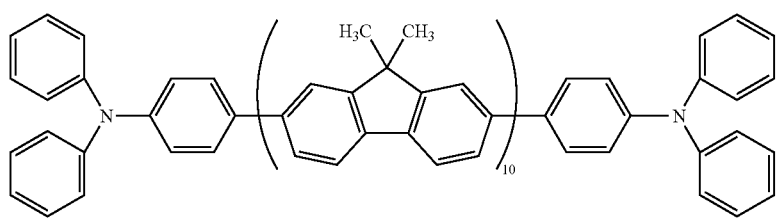
AA-24
<General Formula [IV]>
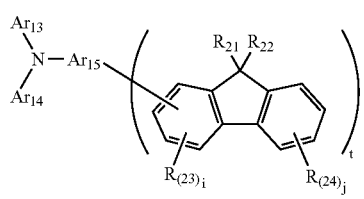
<Examples of Arylamine Compounds of General Formula [IV]>
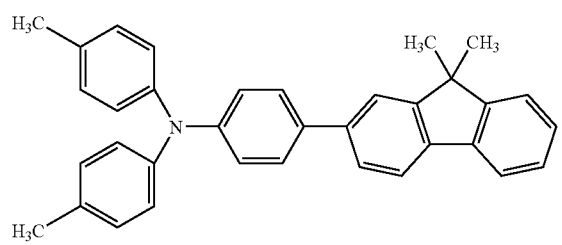
AA-25
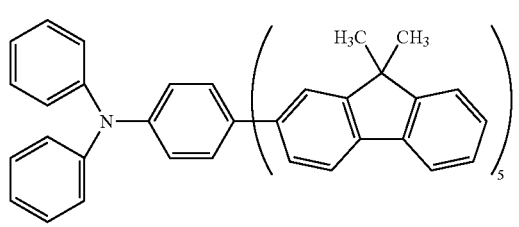
AA-26
-continued
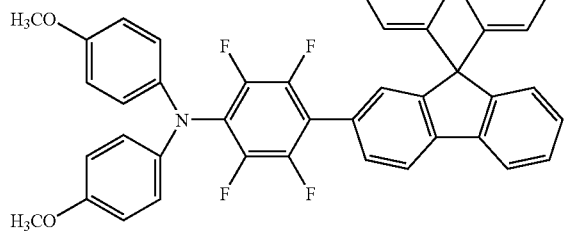
AA-27
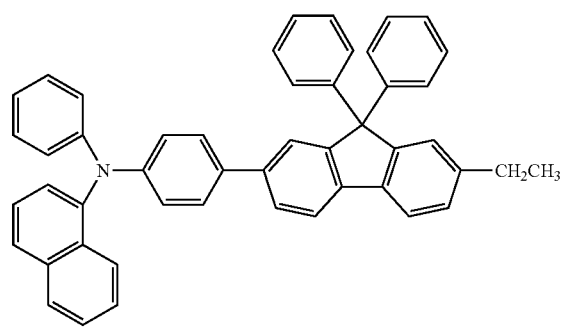
AA-28
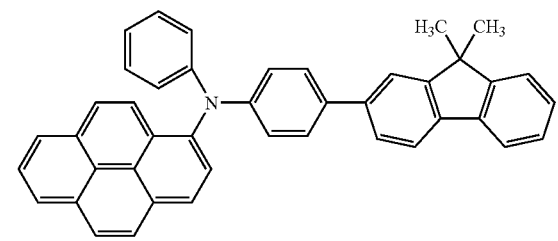
AA-29

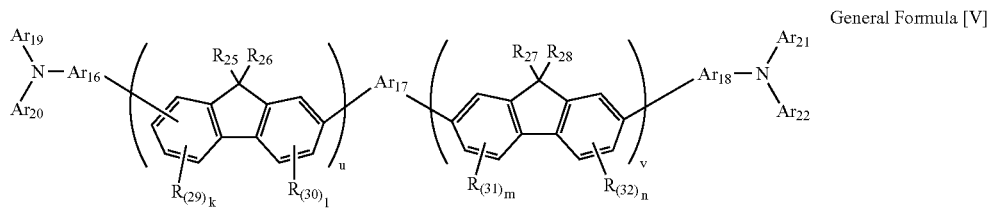
General Formula [V]
<Examples of Arylamine Compounds of General Formula [V]>
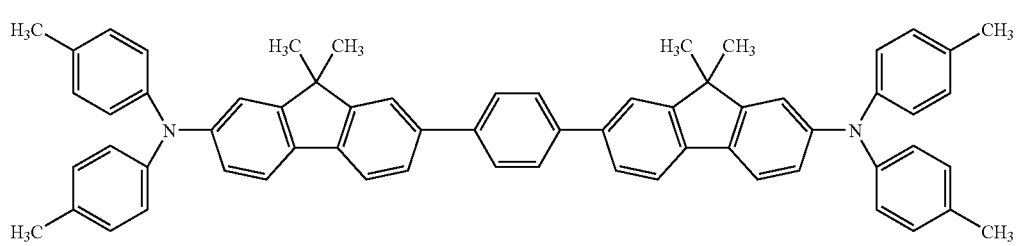
AA-30
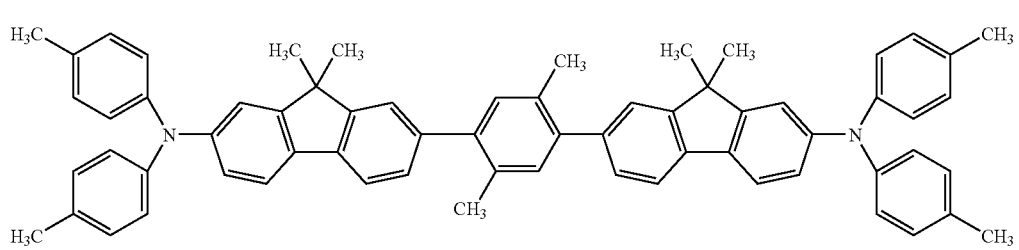
AA-31
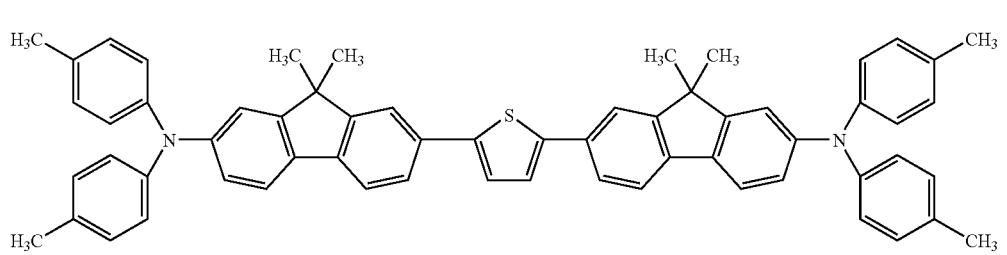
AA-32
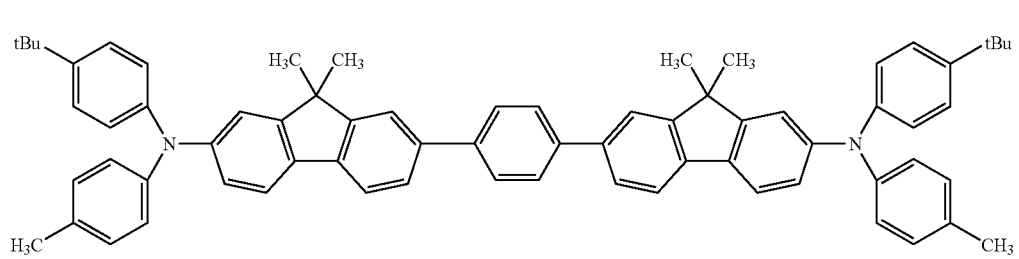
AA-33

-continued
AA-34
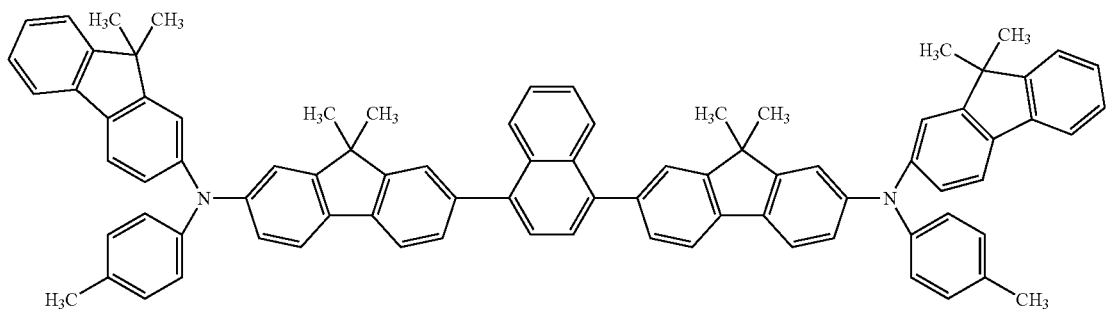
AA-35
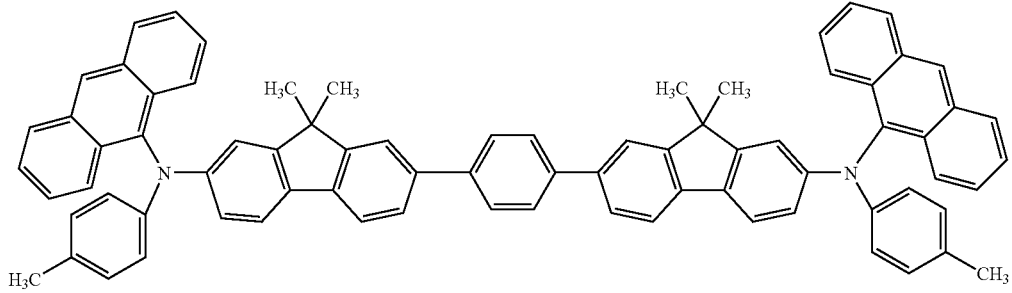
AA-36
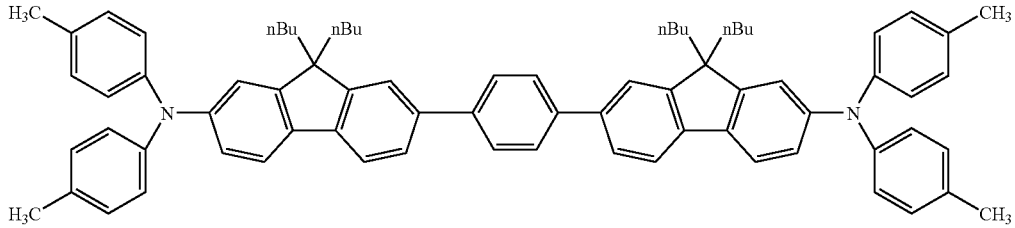
AA-37
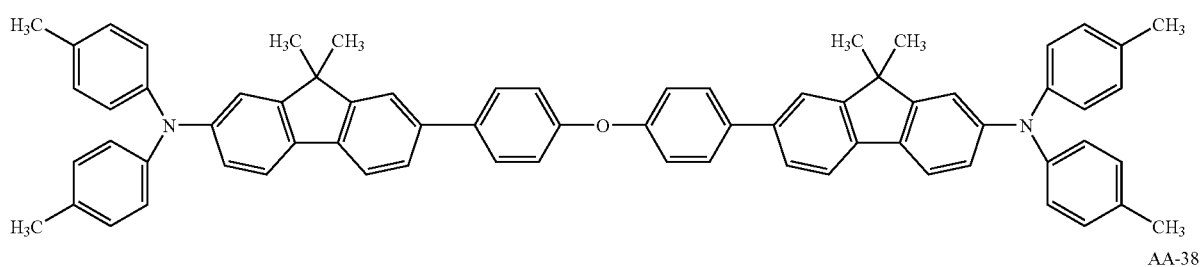
AA-38
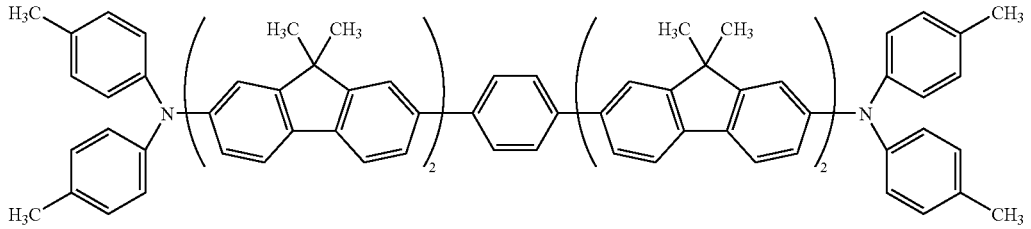
AA-39
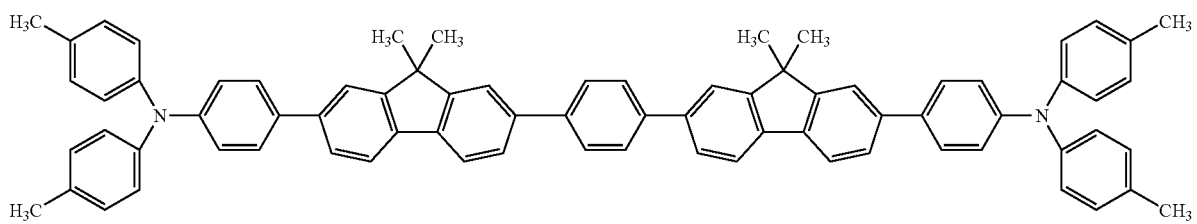

-continued
AA-40
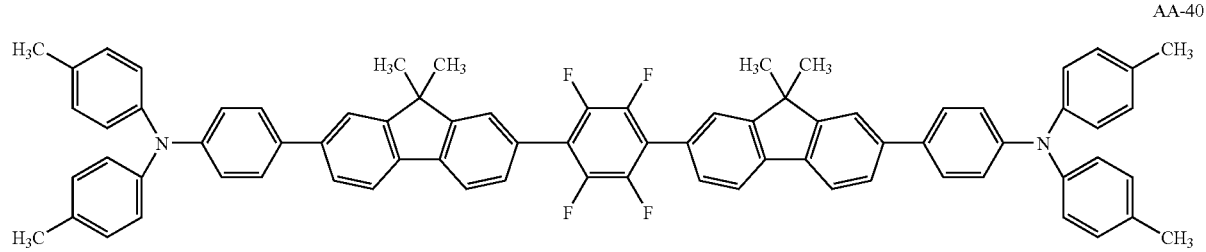
AA-41
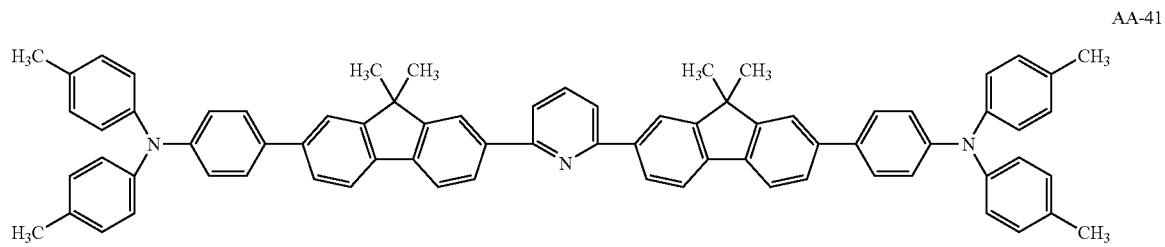
AA-42
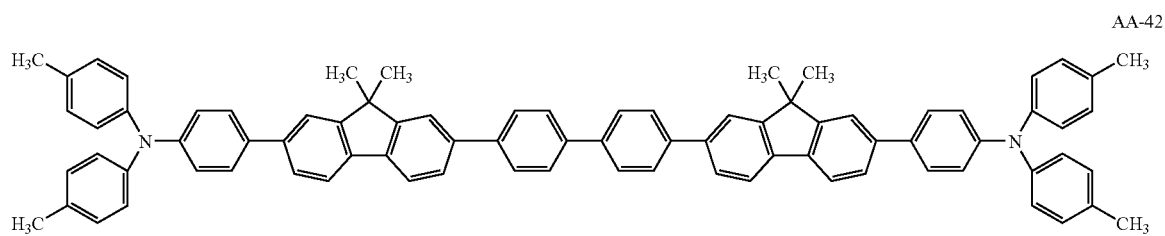
AA-43
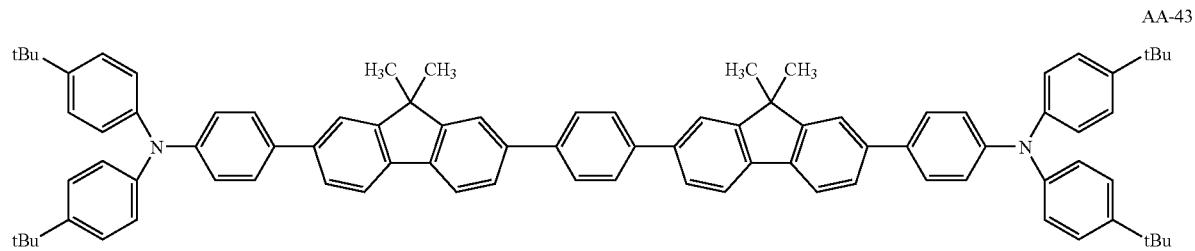
AA-44
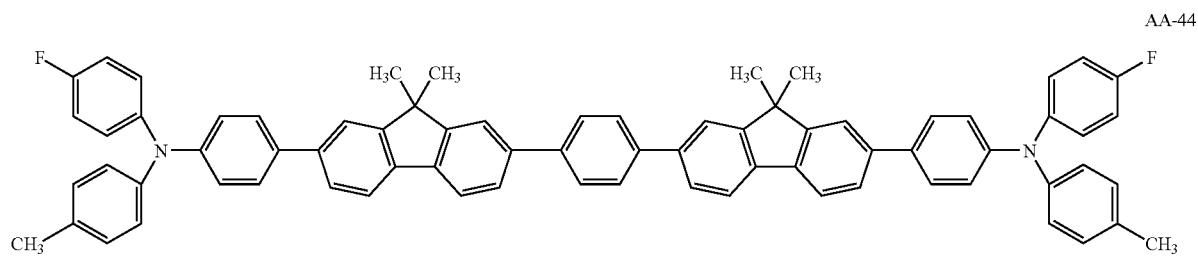
AA-45
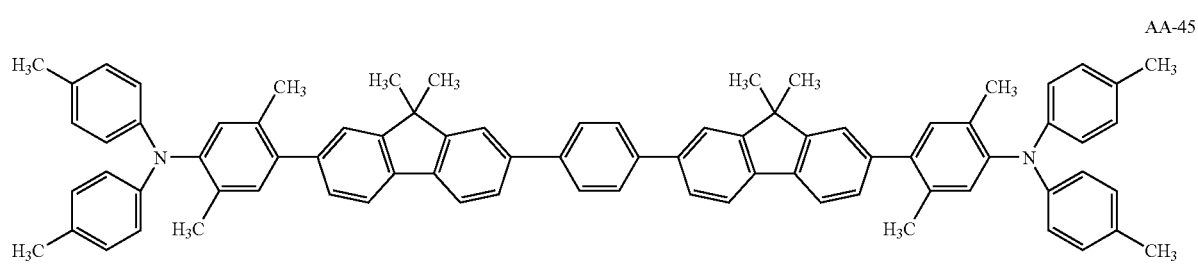

-continued
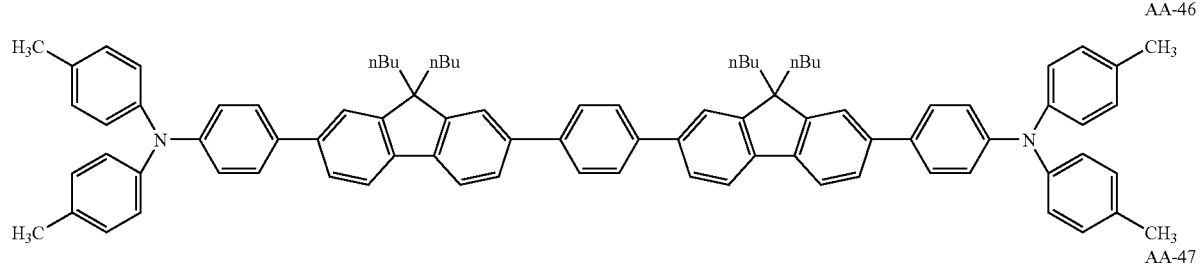
AA-46
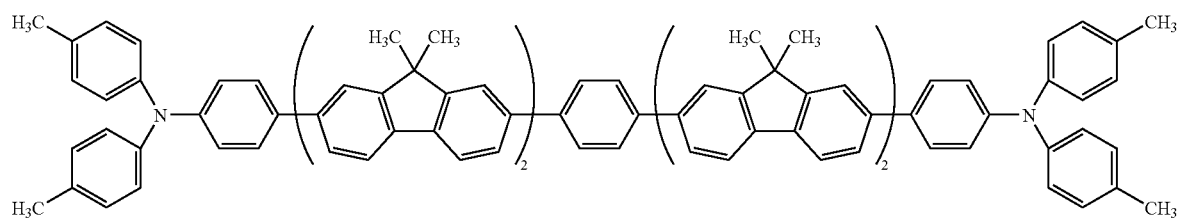
AA-47
<General Formula [VI]>
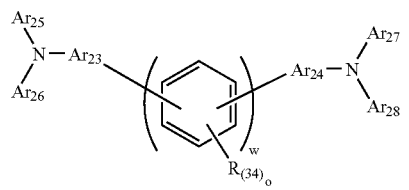
<Examples of Arylamine Compounds of General Formula [VI]>
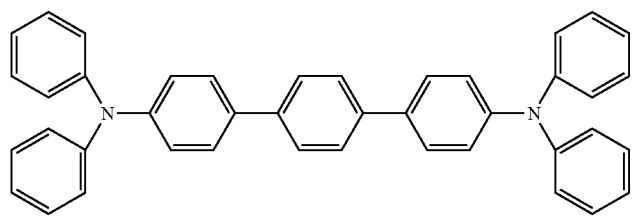
AA-48
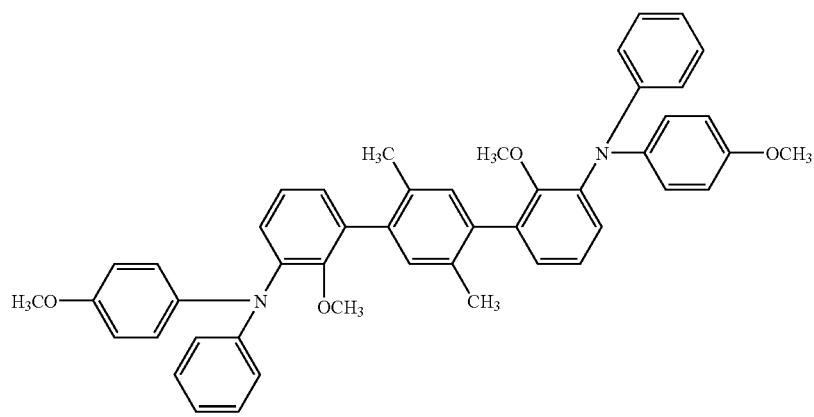
AA-49

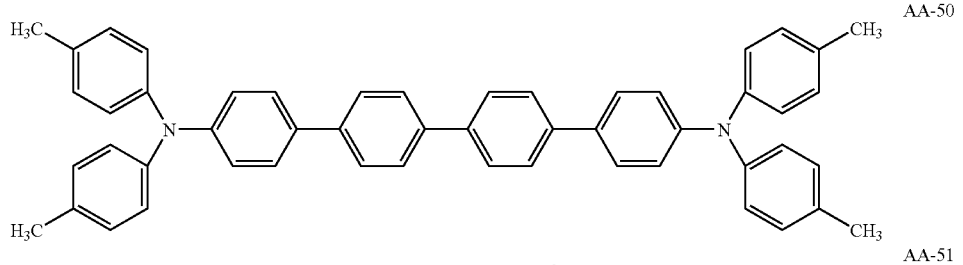
AA-50
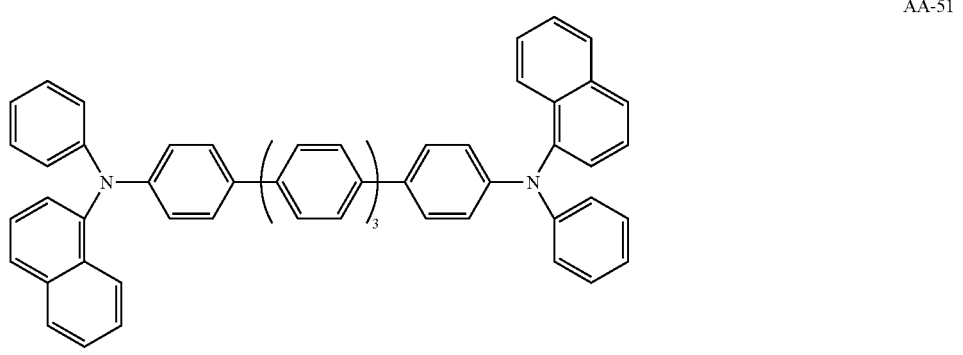
AA-51
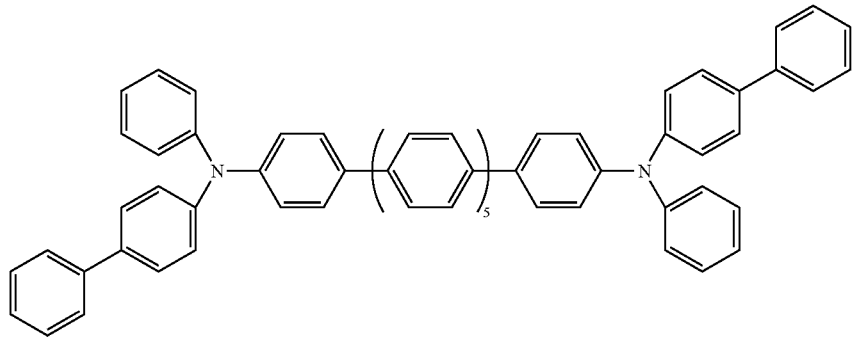
AA-52
<General Formula [VII]>
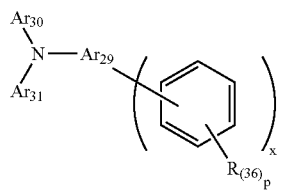
<Examples of Arylamine Compounds of General Formula [VII]>
AA-53
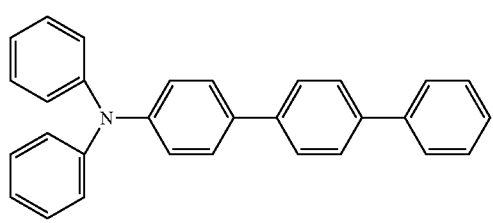
AA-54
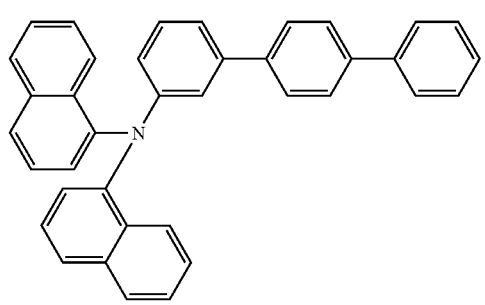
AA-55
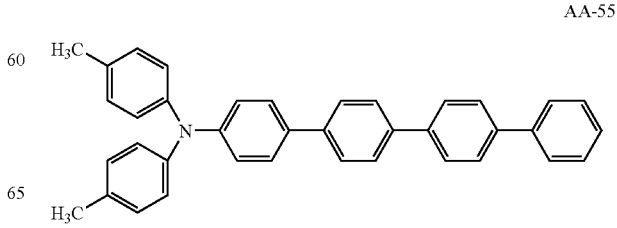

AA-56

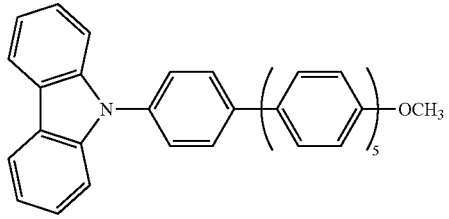

AA-57

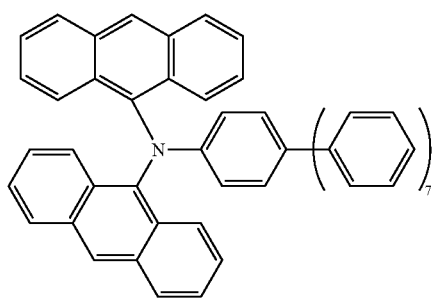

<General Formula [VIII]>

Ar₃₂—(C≡C)ᵧ—Ar₃₃

<Examples of Acetylene Compounds of General Formula [VIII]>

AC-1

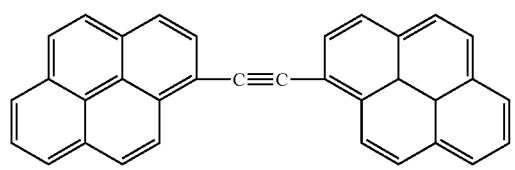

AC-2

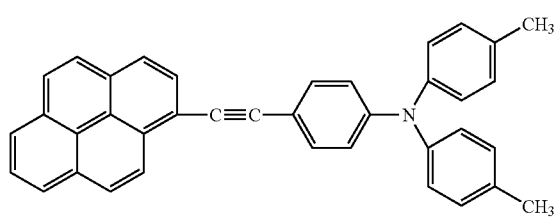

AC-3

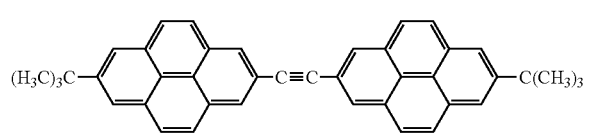

AC-4

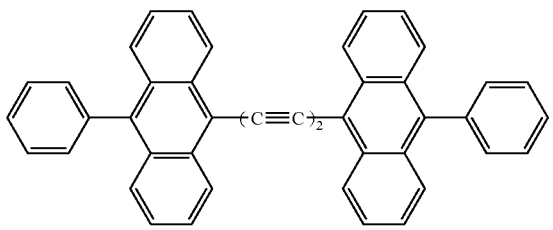

AC-5

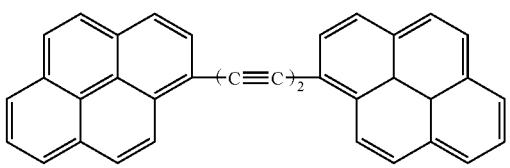

The content ratio of the fluorene compound represented by the general formula [I], and the arylamine compound represented by the general formulae [II] to [VII] or the acetylene compound represented by the general formula [VIII] is such that the arylamine compound or the acetylene compound is used in an amount of preferably 0.01 to 80 parts by weight, more preferably 1 to 40 parts by weight per 100 parts by weight of the fluorene compound.

FIGS. 1 to 7 show preferable examples of the organic light-emitting device of the present invention. In FIGS. 1 to 7, reference numeral 1 denotes a substrate, reference numeral 2 denotes an anode, reference numeral 3 denotes a light-emitting layer, reference numeral 4 denotes a cathode, reference numeral 5 denotes a hole-transporting layer, reference numeral 6 denotes an electron-transporting layer, reference numeral 7 denotes a hole-injecting layer, and reference numeral 8 denotes a hole/exciton blocking layer.

FIG. 1 is a cross-sectional view showing an example of the organic light-emitting device of the present invention. In FIG. 1, the device is composed of an anode 2, a light-emitting layer 3, and a cathode 4, which are provided on a substrate 1 in the mentioned order. The light-emitting device with this structure is advantageous when a compound having by itself a hole-transporting property, an electron-transporting property and a light-emitting property is used or when plural kinds of compounds possessing the respective properties are used as a mixture.

Figure 2:
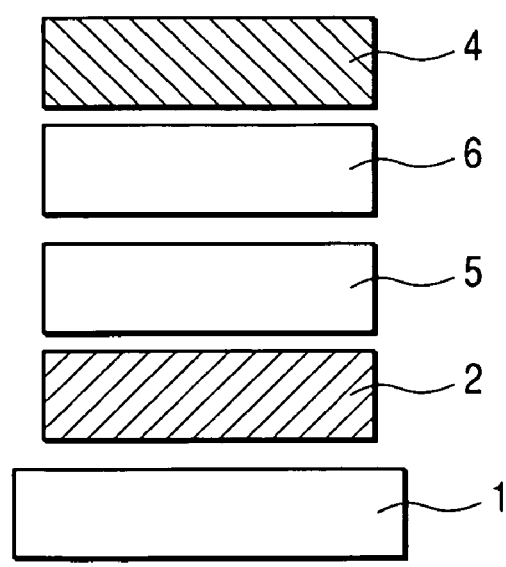
FIG. 2 is a cross-sectional view showing another example of the organic light-emitting device in accordance with the present invention.

FIG. 2 is a cross-sectional view showing another example of the organic light-emitting device of the present invention. In FIG. 2, the device is composed of an anode 2, a hole-transporting layer 5, an electron-transporting layer 6, and a cathode 4, which are provided on a substrate 1 in the mentioned order. In this case, a light-emitting material having either or both of a hole-transporting property and an electron-transporting property is advantageously used for the corresponding one of the layers, in combination with a hole-transporting material or an electron-transporting material having no light-emitting property for the other layer. Incidentally, in this case, the light-emitting layer is composed of either of the hole-transporting layer 5 or the electron-transporting layer 6.

Figure 3:
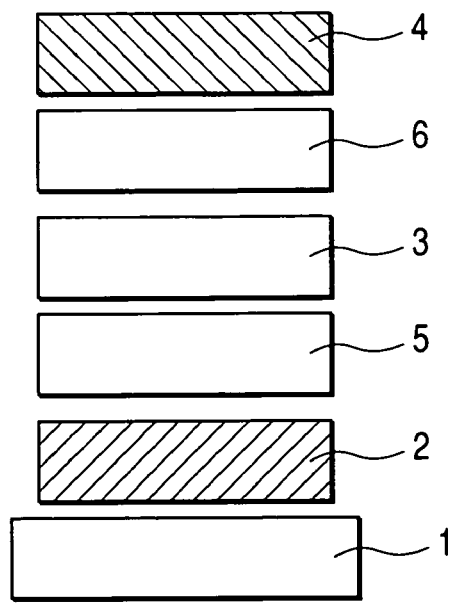
FIG. 3 is a cross-sectional view showing still another example of the organic light-emitting device in accordance with the present invention.

FIG. 3 is a cross-sectional view showing still another example of the organic light-emitting device of the present invention. In FIG. 3, the device is composed of an anode 2, a hole-transporting layer 5, a light-emitting layer 3, an electron-transporting layer 6, and a cathode 4, which are provided on a substrate 1 in the mentioned order. With this arrangement, the carrier-transporting function and the light-emitting function are separated from each other, and compounds having a hole-transporting property, an electron-transporting property, and a light-emitting property respectively are used appropriately in combination therewith. Thus, the degree of freedom in selection of materials greatly increases, and various kinds of compounds having different emission wavelengths can be used, thus allowing a variety of emission hues to be achieved. Furthermore, it also becomes possible to improve the emission efficiency by effectively confining carriers or excitons within the middle light-emitting layer 3.

Figure 4:
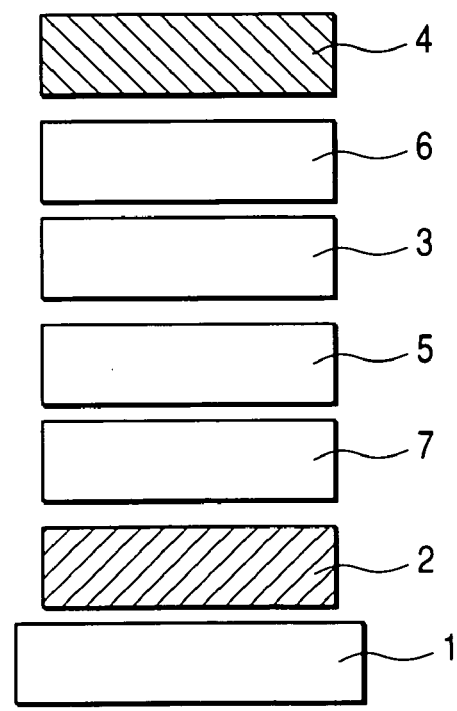
FIG. 4 is a cross-sectional view showing yet another example of the organic light-emitting device in accordance with the present invention.

FIG. 4 is a cross-sectional view showing still another example of the organic light-emitting device of the present invention. In FIG. 4, as compared with the example shown in FIG. 3, the device is constructed such that a hole-injecting layer 7 is provided on the anode 2 side, which is effective for improving adhesion between the anode 2 and the hole-transporting layer 5 or improving the hole-injecting property. Thus, this arrangement is effective for lowering the driving voltage.

Figure 5:
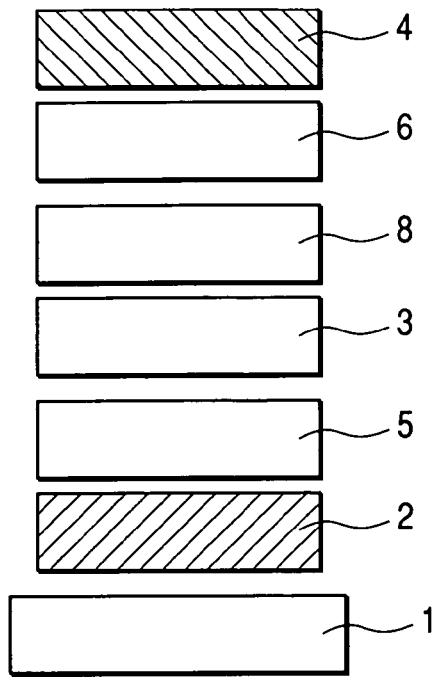
FIG. 5 is a cross-sectional view showing still a further example of the organic light-emitting device in accordance with the present invention.
Figure 6:
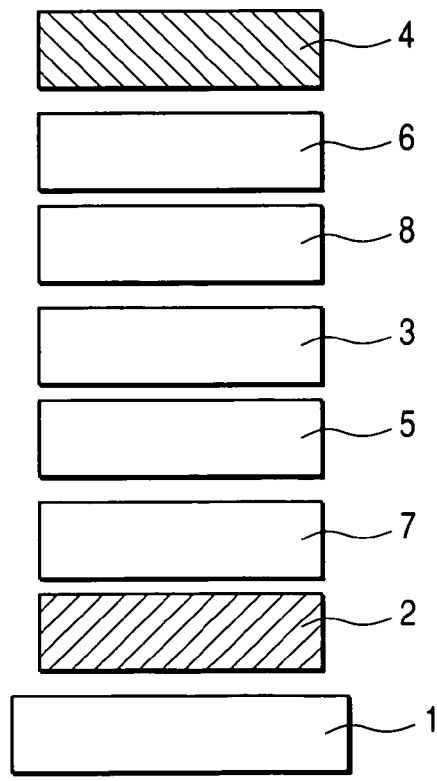
FIG. 6 is a cross-sectional view showing yet another example of the organic light-emitting device in accordance with the present invention.

FIGS. 5 and 6 are cross-sectional views showing other examples of the organic light-emitting device of the present invention, respectively. In FIGS. 5 and 6, as compared with the examples shown in FIGS. 3 and 4, the device is constructed such that a layer (a hole-blocking layer 8) serving to prevent holes or excitons from passing to the cathode 4 side is provided between the light-emitting layer 3 and the electron-transporting layer 6. The use of a compound having an extremely high ionization potential for the hole-blocking layer 8 is effective for improving the emission efficiency.

Figure 7:
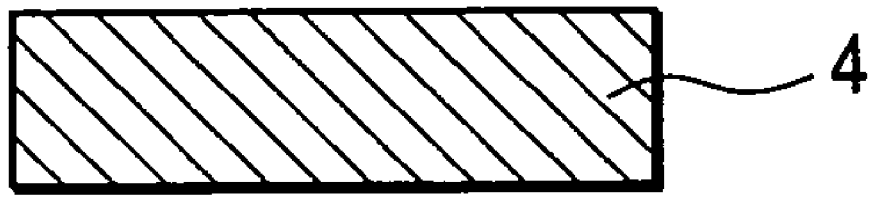
FIG. 7 is a cross-sectional view showing yet still another example of the organic light-emitting device in accordance with the present invention.
Figure 7:
Figure 7:
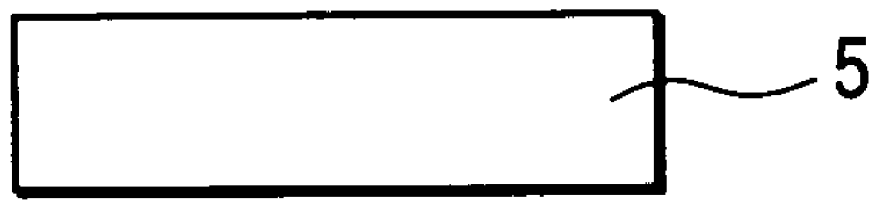
Figure 7:
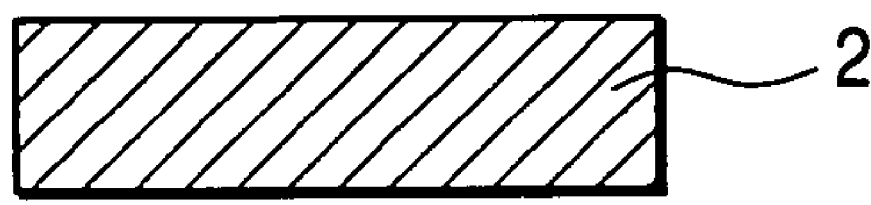
Figure 7:

FIG. 7 is a cross-sectional view showing still another example of the organic light-emitting device of the present invention. In FIG. 7, the device is composed of an anode 2, a hole-transporting layer 5, a light-emitting layer 3, and a cathode 4, which are provided on a substrate 1 in the mentioned order. The light-emitting device with this structure is advantageous when a light-emitting material having by itself either or both of a hole-transporting property and an electron-transporting property is used for the corresponding layers, in combination with a mere hole-transporting material having no light-emitting property.

Note that, in FIGS. 1 to 7, there are shown common basic device structures. The structure of the organic light-emitting device using the compound of the present invention is not limited thereto. For example, it is possible to adopt various layer structures such as one in which an insulating layer is provided at an interface between an electrode and an organic layer, one in which an adhesive layer or an interference layer is additionally provided, and one in which a hole-transporting layer is composed of two layers with different ionization potentials.

The fluorene compound represented by the general formula [I] used in the present invention is a compound superior to the conventional compounds in electron-transporting property and durability, and can be used in any one of the embodiments shown in FIGS. 1 to 7.

In the present invention, the fluorene compound represented by the general formula [I] is used as a component for an electron-transporting layer or a light-emitting layer. However, hitherto known hole-transporting compounds, light-emitting compounds, electron-transporting compounds, or the like may be used in combination therewith as needed.

Examples of those compounds will be given below.

<Hole-Transporting Compounds>

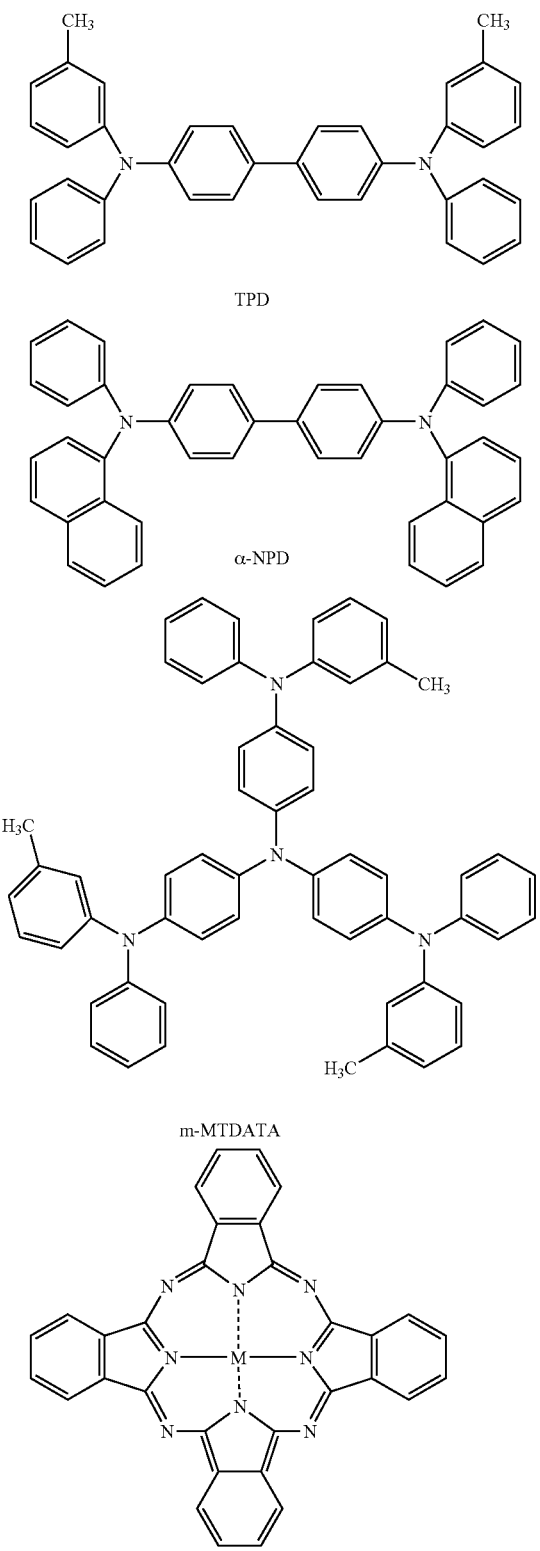

-continued
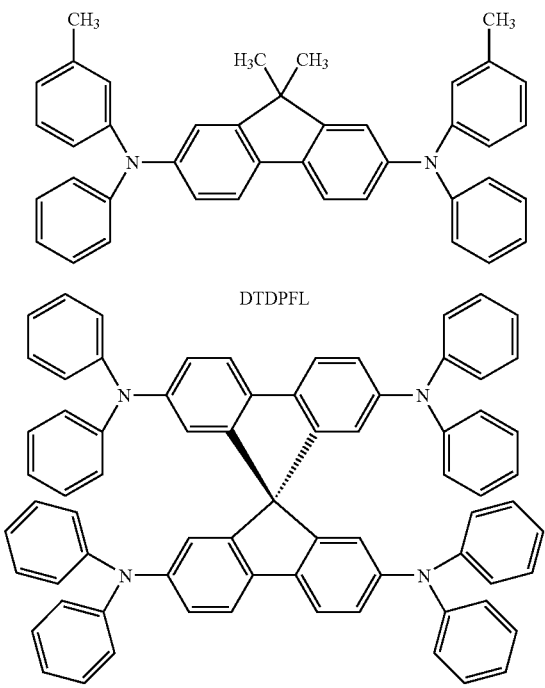
DTDPFL
spiro-TPD
TPAC
PDA
<Electron-transporting/Light-Emitting Compounds>
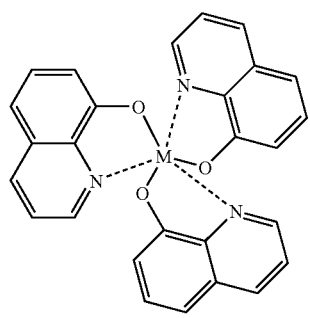
M: Al, Ga
-continued
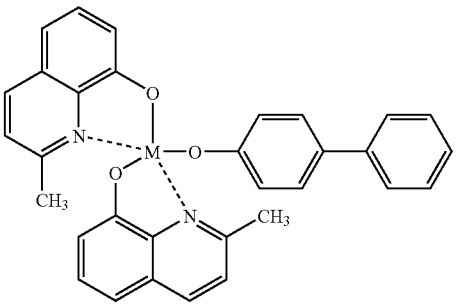
M: Al, Ga
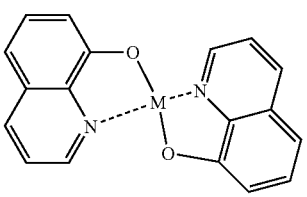
M: Zn, Mg, Be
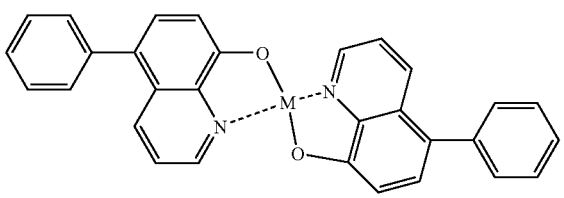
M: Zn, Mg, Be
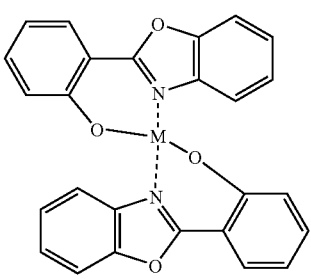
M: Zn, Mg, Be
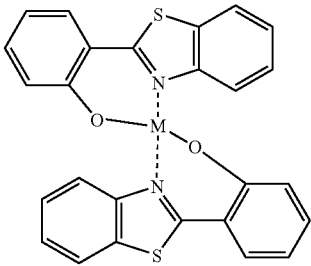
M: Zn, Mg, Be

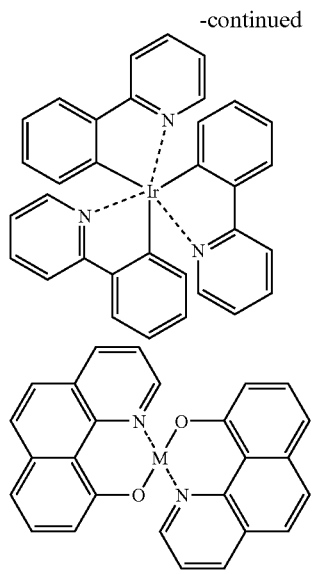
M: Zn, Mg, Be
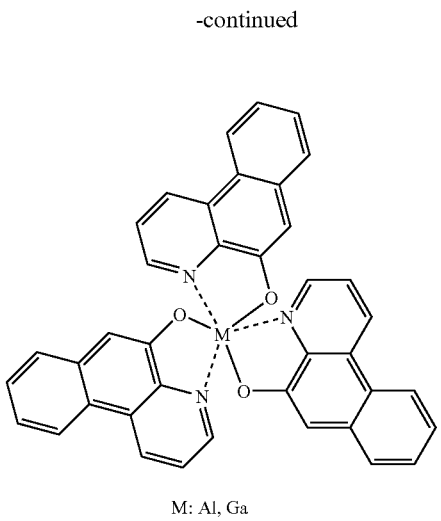
M: Al, Ga
<Light-Emitting Compounds>
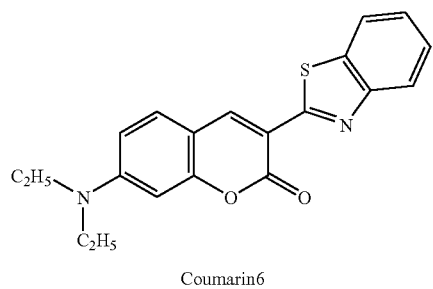
Coumarin6
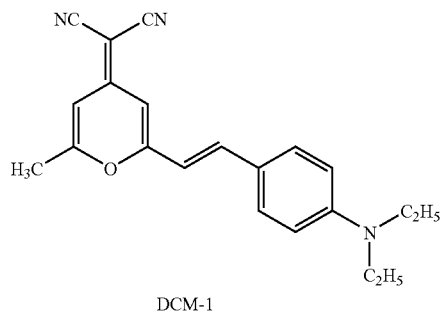
DCM-1
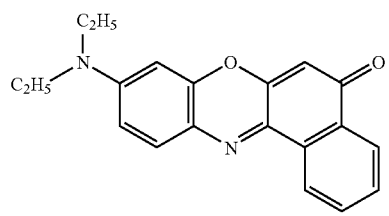
Nile red
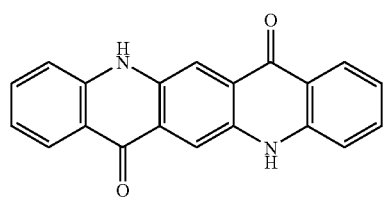
Quinacridone
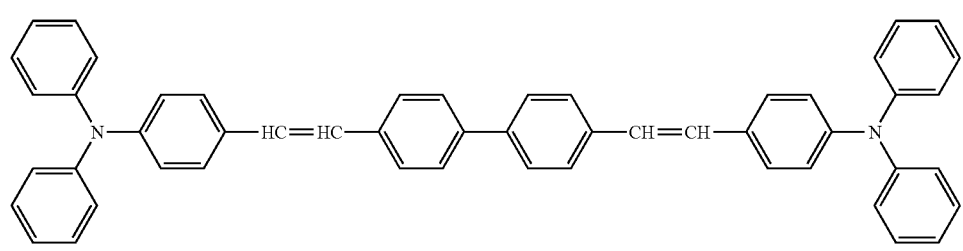
DTPABVi

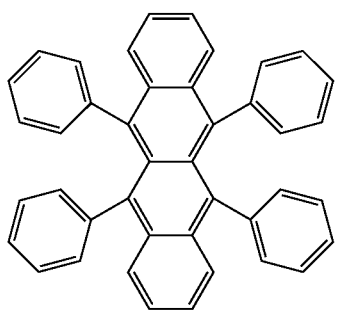
Rubrene
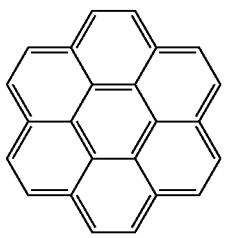
Coronene
<Light-Emitting Layer Matrix Compounds and Electron-Transporting Compounds>
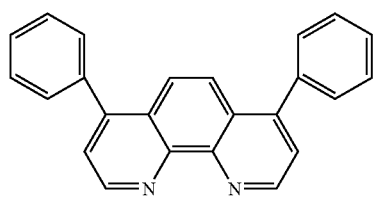
BPhen
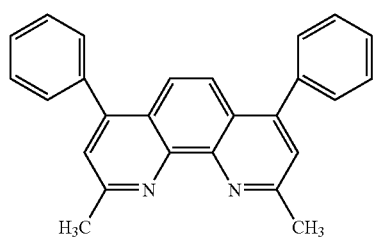
BCP
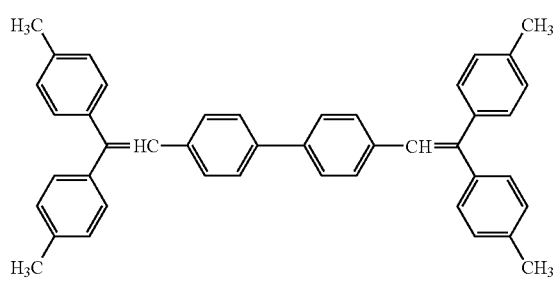
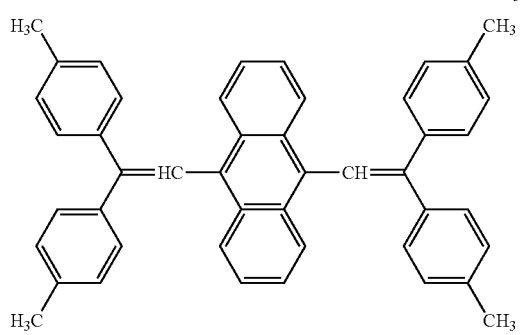
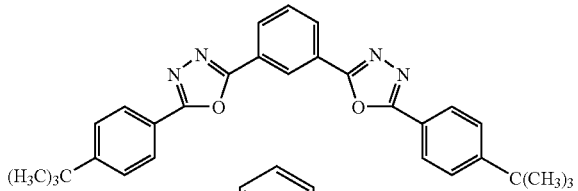
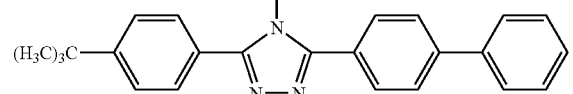
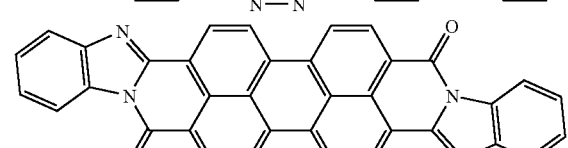
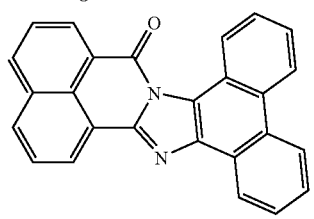
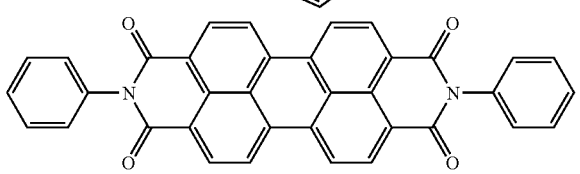
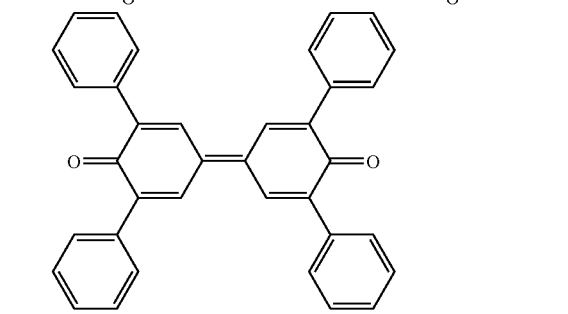

<Polymeric Hole-Transporting Compounds>
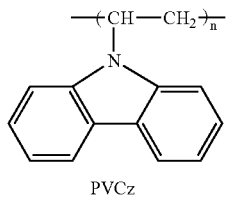
PVCz
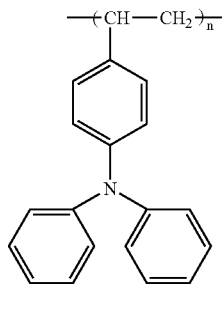
DPA-PS
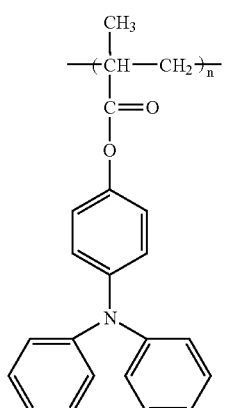
TPA-PMMA
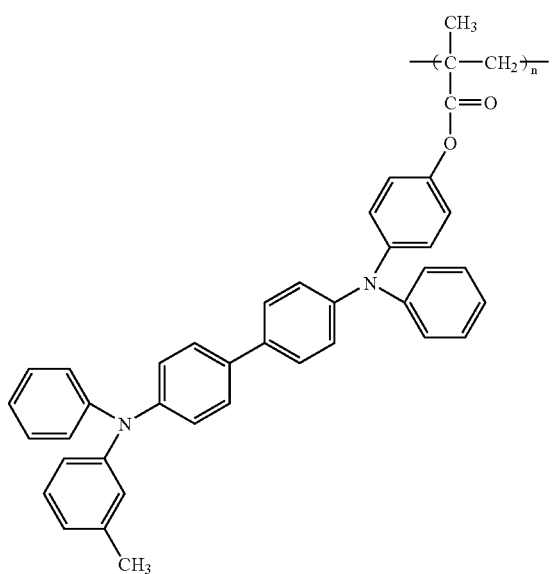
TPD-PMAA
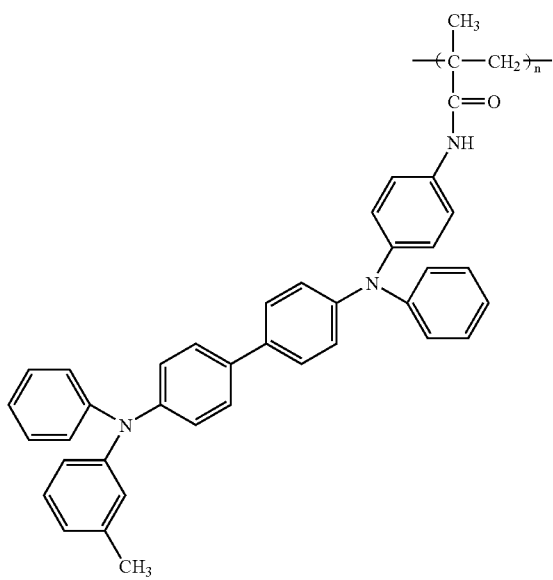
TPD-PMAA

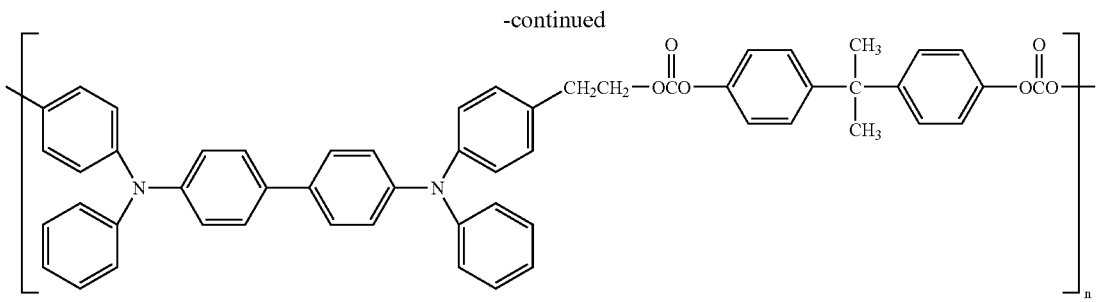

TPD-PCA

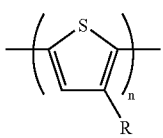

R: C$_6$H$_{13}$, C$_8$H$_{17}$, C$_{12}$H$_{25}$
Poly thiophene

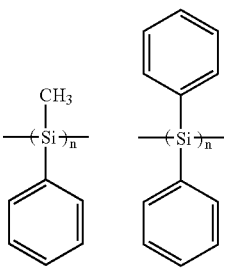

Polysilane

<Polymeric Light-Emitting Compounds and Charge-Transporting Compounds>

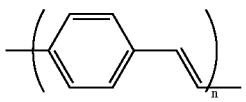

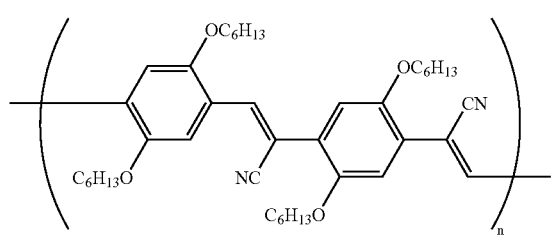

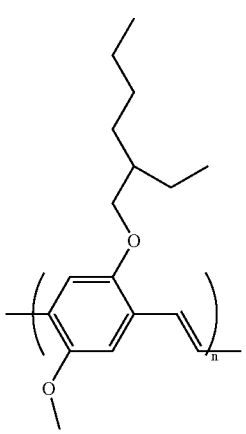

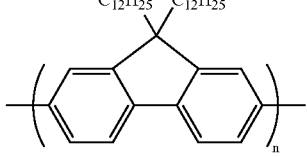

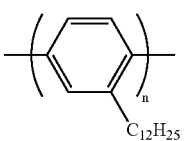

In the organic light-emitting device of the present invention, the layer(s) containing the fluorene compound represented by the general formula [I] and the layer(s) containing other organic compound(s) are generally formed as thin films by a vacuum evaporation method or by an application method after dissolving in an appropriate solvent. In particular, in the case of forming a film with the application method, the film may be formed by additionally using an appropriate binder resin.

The binder resin can be selected from a wide variety of binder resins including, for example, polyvinyl carbazole resin, polycarbonate resin, polyester resin, polyarylate resin, polystyrene resin, acrylic resin, methacrylic resin, butyral resin, polyvinyl acetal resin, diallyl phthalate resin, phenolic resin, epoxy resin, silicone resin, polysulfone resin, and urea resin, although it is not limited thereto. In addition, one of the above resins may be used singularly, or two or more such resins may be combined with each other as a copolymer.

Preferably, the anode material has a work function that is as large as possible. For example, an elemental metal such as gold, platinum, nickel, palladium, cobalt, selenium, or vanadium, or an alloy thereof, or a metal oxide such as tin oxide, zinc oxide, indium tin oxide (ITO), or indium zinc oxide can be used. In addition, a conductive polymer such as polyaniline, polypyrrole, polythiophene, or polyphenylene sulfide can be also used. Any one of those electrode materials may be used singularly or plural electrode materials may be used in combination.

On the other hand, preferably, the cathode material may have a small work function. For example, an elemental metal such as lithium, sodium, potassium, cesium, calcium, magnesium, aluminum, indium, silver, lead, tin, or chromium, or an alloy of plural metals can be used therefor. It is also possible to use a metal oxide such as indium tin oxide (ITO). In addition, the cathode may take either a single-layer structure or a multi-layer structure.

The substrate used in the present invention may be, although not particularly limited, a non-transparent substrate such as a metallic substrate or a ceramic substrate, or a transparent substrate formed of glass, quartz, plastic sheet, or the like. In addition, it is also possible to control the emission color by using a color filter film, a fluorescent color-changing filter film, a dielectric reflection film or the like for the substrate.

Furthermore, a protective layer or an encapsulating layer may also be provided on the prepared device for preventing the device from coming into contact with oxygen, moisture, or the like. The protective layer may be a diamond thin film, a film made of an inorganic material such as a metal oxide or a metal nitride, or a polymer film made of fluororesin, polypara-xylylene, polyethylene, silicone resin, polystyrene resin or the like. In addition, a photocurable resin or the like can be used therefor. Furthermore, it is also possible to cover the device with glass, a gas-impermeable film, a metal or the like or package the device itself with an appropriate encapsulating resin

EXAMPLES

The present invention will now be described in more detail based on examples. However, the present invention is not limited to those examples.

Synthesis Example 1

[Synthesis of Exemplified Compound No. 1]

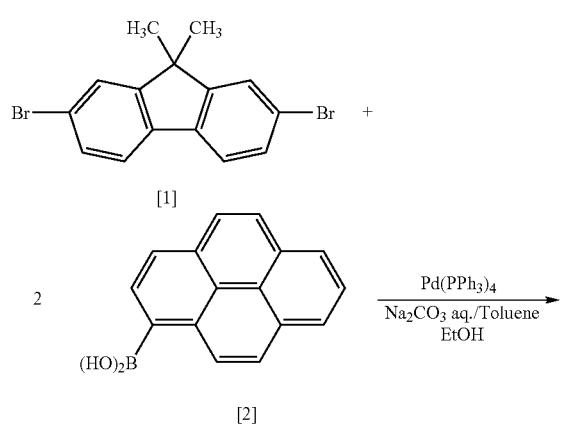

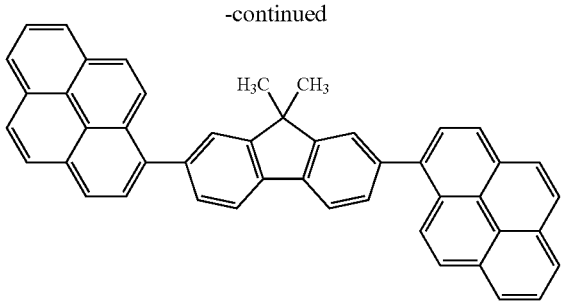

To a 500-ml three-neck flask, 2.0 g (5.68 mmol) of 2,7-dibromo-9,9-dimethylfluorene [1], 4.2 g (17.0 mmol) of pyrene-1-boronic acid [2], 120 ml of toluene, and 60 ml of ethanol were added. Then, an aqueous solution of 24 g of sodium carbonate in 120 ml of water was added dropwise therein with stirring in a nitrogen atmosphere at room temperature, followed by the addition of 0.33 g (0.28 mmol) of tetrakis (triphenylphosphine) palladium (0). After stirring the mixture for 30 minutes at room temperature, the temperature was raised to 77° C., followed by stirring for 5 hours. After the reaction, an organic layer was extracted with chloroform and then dried with anhydrous sodium sulfate, followed by purification with a silica gel column (hexane and toluene mixture developing solvent). Consequently, 3.0 g (89% yield) of a compound [3] (white crystal) was obtained.

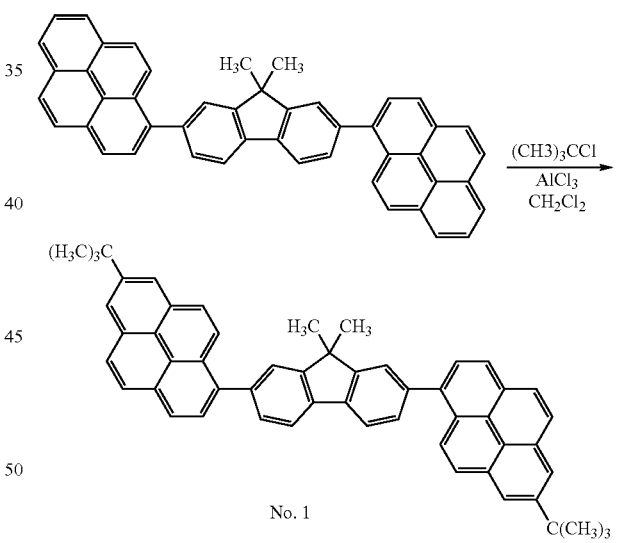

To a 500-ml three-neck flask, 3.51 g (5.89 mmol) of compound [3], 1.64 g (17.67 mmol) of tert-butyl chloride and 200 ml of dichloromethane were added. The resultant mixture was stirred at 0° C., and then 1.71 g (13.0 mmol) of aluminum chloride was slowly added thereto. After stirring the mixture for 30 minutes at 0° C., the temperature was raised to room temperature, followed by stirring for 5 hours. After the reaction, an organic layer was taken into 200 ml of water, extracted with chloroform and then dried with anhydrous sodium sulfate, followed by purification with a silica gel column (hexane and toluene mixture developing solvent). Consequently, 3.53 g (84% yield) of exemplified compound No. 1 (white crystal) was obtained.

Synthesis Example 2

[Synthesis of Exemplified Compound No. 14]

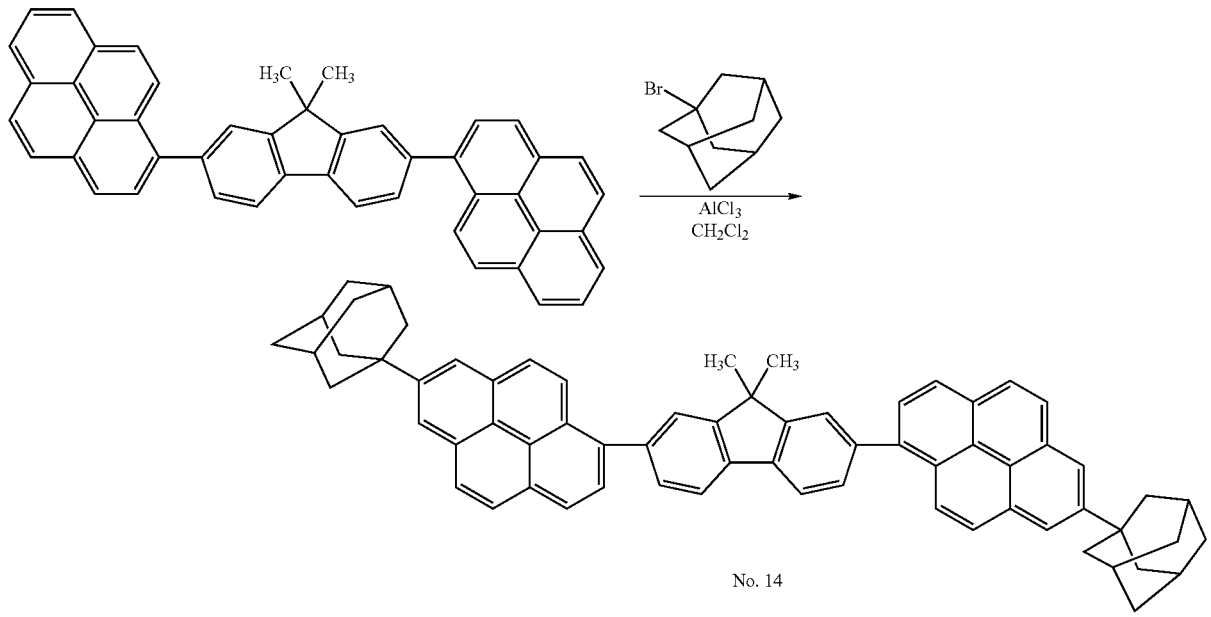

No. 14

To a 500-ml three-neck flask, 1.50 g (2.52 mmol) of compound [3], 1.61 g (7.55 mmol) of 1-bromoadamantane and 100 ml of dichloromethane were added. The resultant mixture was stirred at 0° C., and then 0.70 g (5.30 mmol) of aluminum chloride was slowly added thereto. After stirring the mixture for 30 minutes at 0° C., the temperature was raised to room temperature, followed by stirring for 5 hours. After the reaction, an organic layer was taken into 200 ml of water, extracted with chloroform and then dried with anhydrous sodium sulfate, followed by purification with a silica gel column (hexane and toluene mixture developing solvent). Consequently, 1.42 g (65% yield) of exemplified compound No. 14 (white crystal) was obtained.

Example 1

A device having the structure shown in FIG. 2 was prepared.

On a glass substrate as the substrate 1, indium tin oxide (ITO) was deposited to form a film with a thickness of 120 nm by sputtering method to obtain the anode 2, so that the substrate thus formed was used as a transparent conductive support substrate. The substrate was subjected to ultrasonic cleaning sequentially with acetone and with isopropyl alcohol (IPA). Following this, the substrate was washed with IPA through boiling and then dried. Furthermore, the substrate after UV/ozone cleaning was used as the transparent conductive support substrate.

On the transparent conductive support substrate, a chloroform solution of the compound represented by the following structural formula was applied to form a film of 30 nm in thickness by a spin-coating method, thereby forming the hole-transporting layer 5.

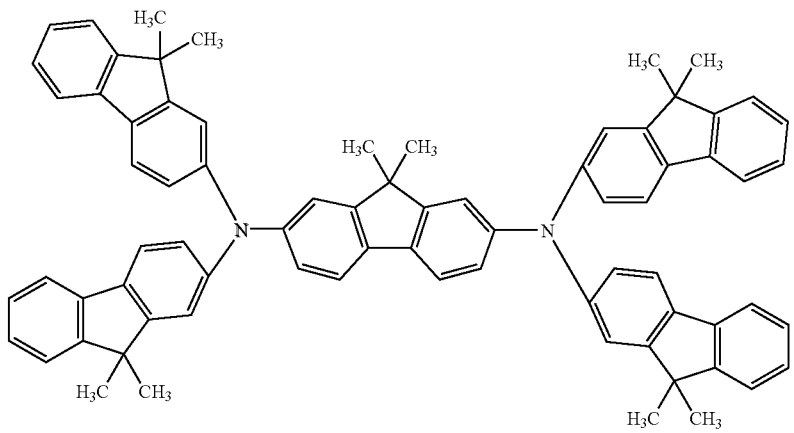

Furthermore, a fluorene compound represented as exemplified compound No. 1 was deposited to form a film of 50 nm in thickness by vacuum evaporation method, thereby forming the electron-transporting layer 6. The film formation was performed under the conditions such that the degree of vacuum at the time of evaporation was $1.0 \times 10^{-4}$ Pa and the film formation rate was 0.2 to 0.3 nm/sec.

Next, a metal layer film of 50 nm in thickness was formed on the above organic layer as the cathode 4 using an evaporation material made of aluminum and lithium (lithium concentration: 1 atomic %) by vacuum evaporation method, and further an aluminum layer of 150 nm in thickness was formed by vacuum evaporation method. The film formation was performed under the conditions such that the degree of vacuum at the time of evaporation was $1.0 \times 10^{-4}$ Pa and the film formation rate was 1.0 to 1.2 nm/sec.

Furthermore, the resultant structure was covered with a protective glass plate in a nitrogen atmosphere and was then encapsulated with an acrylic resin adhesive.

When a DC voltage of 4 V was applied to the device thus obtained with the ITO electrode (anode 2) being connected to a positive electrode and the Al—Li electrode (cathode 4) being connected to a negative electrode, an electric current flowed through the device at a current density of $38.5$ mA/cm$^2$ and light emission of a blue color at a luminance of 900 cd/m$^2$ was observed.

Furthermore, when the current density was kept at 50.0 mA/cm$^2$ and the voltage was applied for 100 hours, the deterioration of luminance was small; an initial luminance of 1000 cd/m$^2$ was reduced to a luminance of 950 cd/m$^2$ after 100 hours.

Examples 2 to 4

Devices were prepared and evaluated following the same procedure as in Example 1 with the exception that the compounds shown in Table 2 were used in place of exemplified compound No. 1. The results are shown in Table 1.

Comparative Examples 1 and 2

Devices were prepared and evaluated following the same procedure as in Example 1 with the exception that compounds represented by the following structural formulae were used in place of exemplified compound No. 1. The results are shown in Table 1.

TABLE 1

<Comparative Compound No. 1>

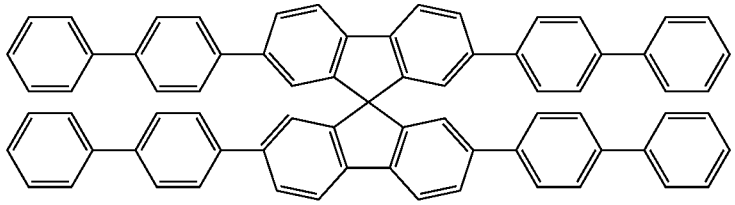

<Comparative Compound No. 2>

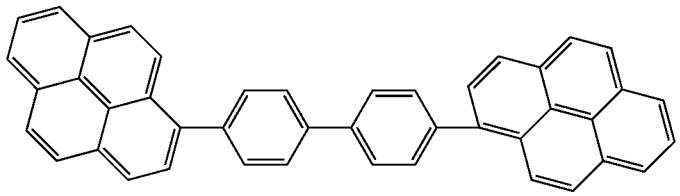

| | | Initial Stage | | Durability | |
| | | | | | Luminance |
| Example No. | Exemplified Compound No. | Applied Voltage (V) | Luminance (cd/m$^2$) | Current Density (mA/cm$^2$) | Initial Luminance (cd/m$^2$) | After 100 Hours (cd/m$^2$) |
|---|---|---|---|---|---|---|
| Example 1 | 1 | 4 | 900 | 50.0 | 1000 | 950 |
| Example 2 | 2 | 4 | 890 | 50.0 | 980 | 940 |
| Example 3 | 7 | 4 | 870 | 50.0 | 950 | 890 |
| Example 4 | 12 | 4 | 850 | 50.0 | 910 | 860 |
| Comparative Example 1 | Comparative Compound 1 | 4 | 400 | 50.0 | 450 | 200 |
| Comparative Example 2 | Comparative Compound 2 | 4 | 380 | 50.0 | 400 | 150 |

Example 5

A device having the structure shown in FIG. 3 was prepared.

Similarly to Example 1, a hole-transporting layer 5 was formed on a transparent conductive support substrate.

Further, a fluorene compound represented by exemplified compound No. 1 was deposited to form a film of 20 nm in thickness by vacuum evaporation method, thereby forming a light-emitting layer 3. The film formation was performed under the conditions such that the degree of vacuum at the time of evaporation was $1.0 \times 10^{-4}$ Pa and the film formation rate was 0.2 to 0.3 nm/sec.

Furthermore, bathophenanthroline (Bpen) was deposited into a film of 40 nm in thickness by vacuum evaporation method, thereby forming an electron-transporting layer 6. The film formation was performed under the conditions such that the degree of vacuum at the time of evaporation was $1.0 \times 10^{-4}$ Pa and the film formation rate was 0.2 to 0.3 nm/sec.

Next, in the same manner as in Example 1, a cathode 4 was formed and the resultant structure was then encapsulated.

When a DC voltage of 4 V was applied to the device thus obtained with the ITO electrode (anode 2) being connected to a positive electrode and the Al—Li electrode (cathode 4) being connected to a negative electrode, an electric current flowed through the device at a current density of 70.0 mA/cm$^2$ and light emission of a blue color at a luminance of 11000 cd/m$^2$ was observed.

Furthermore, when a voltage was applied for 100 hours with the current density being kept at 100.0 mA/cm$^2$, the deterioration of luminance was small such that an initial luminance of 13000 cd/m$^2$ was reduced to a luminance of 11000 cd/m$^2$ after 100 hours.

Examples 6 to 8

Devices were prepared and evaluated in the same way as that of Example 5, except that the compounds shown in Table 2 were used in place of the exemplified compound No. 1. The results are shown in Table 2.

Comparative Examples 3 and 4

Devices were prepared and evaluated following the same procedure as in Example 5 with the exception that comparative compounds 1 and 2 were used in place of exemplified compound No. 1. The results are shown in Table 2.

Example 9

A device having the structure shown in FIG. 3 was prepared.

On a transparent conductive support substrate similar to that in Example 1, a chloroform solution of a compound represented by the following structural formula was applied to form a film of 20 nm in thickness by spin-coating method, thereby forming a hole-transporting layer 5.

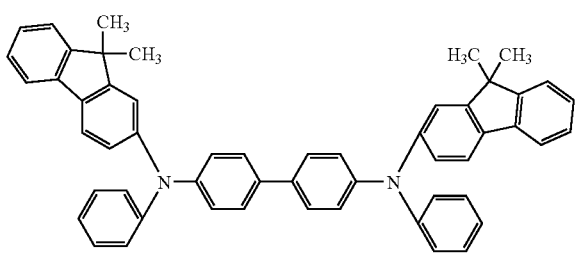

Furthermore, the fluorene compound represented as exemplified compound No. 1 and the arylamine compound represented as exemplified compound No. AA-6 (weight ratio of 100:1) were deposited into a film with a thickness of 20 nm by vacuum evaporation method to form a light-emitting layer 3. The film formation was performed under the conditions such that the degree of vacuum at the time of evaporation was $1.0 \times 10^{-4}$ Pa and the film formation rate was 0.2 to 0.3 nm/sec.

Next, in the same manner as in Example 5, an electron-transporting layer 6 and a cathode 4 were formed and the resultant structure was then encapsulated.

When a DC voltage of 4 V was applied to the device thus obtained with the ITO electrode (anode 2) being connected to a positive electrode and the Al—Li electrode (cathode 4) being connected to a negative electrode, an electric current was flowed through the device at a current density of 75.0 mA/cm$^2$ and light emission of a pure blue color at a luminance of 13000 cd/m$^2$ was observed.

Furthermore, when a voltage was applied for 100 hours while keeping the current density at 80.0 mA/cm$^2$, the dete-

TABLE 2

| | | Initial Stage | | Durability | | Luminance |
| --- | --- | --- | --- | --- | --- | --- |
| Example No. | Exemplified Compound No. | Applied voltage (V) | Luminance (cd/m$^2$) | Current Density (mA/cm$^2$) | Initial Luminance (cd/m$^2$) | After 100 Hours (cd/m$^2$) |
| Example 5 | 1 | 4 | 11000 | 100.0 | 13000 | 11000 |
| Example 6 | 3 | 4 | 10000 | 100.0 | 11000 | 10000 |
| Example 7 | 7 | 4 | 9500 | 100.0 | 8700 | 7500 |
| Example 8 | 12 | 4 | 11000 | 100.0 | 13000 | 11000 |
| Comparative Example 3 | Comparative Compound 1 | 4 | 1800 | 100.0 | 2000 | 900 |
| Comparative Example 4 | Comparative Compound 2 | 4 | 4500 | 100.0 | 5000 | 2100 | rioration of luminance was small such that an initial luminance of 15000 cd/m² was reduced to a luminance of 12000 cd/m² after 100 hours.

Examples 10 to 19

Devices were prepared and evaluated following the same procedure as in Example 9 with the exception that exemplified fluorene compound No. 1 and/or exemplified arylamine compound No. AA-6 were replaced with ones shown in Table 3. The results are shown in Table 3.

Comparative Examples 5 and 6

Devices were prepared and evaluated following the same procedure as in Example 9 with the exception that comparative compounds 1 and 2 were used in place of exemplified compound No. 1. The results are shown in Table 3.

Next, in the same manner as in Example 1, a cathode 4 was formed and the resultant structure was then encapsulated.

When a DC current voltage of 4 V was applied to the device thus obtained with the ITO electrode (anode 2) being connected to a positive electrode and the Al—Li electrode (cathode 4) being connected to a negative electrode, an electric current flowed through the device at a current density of 35.5 mA/cm² and light emission of a blue color at a luminance of 2200 cd/m² was observed.

Furthermore, when a voltage was applied for 100 hours with the current density being kept at 50.0 mA/cm², the deterioration of luminance was small such that an initial luminance of 4100 cd/m² was reduced to a luminance of 3100 cd/m² after 100 hours.

TABLE 3

| Example No. | Exemplified Compound No. | Exemplified Arylamine Compound No. | Initial Stage | | Durability | | |
|---|---|---|---|---|---|---|---|
| | | | Applied Voltage (V) | Luminance (cd/m²) | Current Density (mA/cm²) | Initial Luminance (cd/m²) | Luminance after 100 hours (cd/m²) |
| Example 9 | 1 | AA-6 | 4 | 13000 | 80.0 | 15000 | 12000 |
| Example 10 | 1 | AA-11 | 4 | 13500 | 80.0 | 15200 | 12600 |
| Example 11 | 1 | AA-15 | 4 | 11500 | 80.0 | 13000 | 10100 |
| Example 12 | 1 | AA-25 | 4 | 10200 | 80.0 | 11900 | 10000 |
| Example 13 | 1 | AA-39 | 4 | 12800 | 80.0 | 13800 | 11200 |
| Example 14 | 1 | AA-50 | 4 | 11000 | 80.0 | 12200 | 10800 |
| Example 15 | 1 | AC-1 | 4 | 16200 | 80.0 | 19000 | 16000 |
| Example 16 | 7 | AA-15 | 4 | 13300 | 80.0 | 15100 | 13500 |
| Example 17 | 7 | AA-53 | 4 | 12200 | 80.0 | 14100 | 12200 |
| Example 18 | 12 | AC-1 | 4 | 16500 | 80.0 | 17800 | 16100 |
| Example 19 | 33 | AA-10 | 4 | 13500 | 80.0 | 14300 | 12500 |
| Comparative Example 5 | Comparative Compound 1 | AA-6 | 4 | 4000 | 80.0 | 4500 | 1800 |
| Comparative Example 6 | Comparative Compound 2 | AA-6 | 4 | 3000 | 80.0 | 3500 | 1000 |

Example 20

A device having the structure shown in FIG. 7 was prepared.

On a transparent conductive support substrate which was similar to that of Example 1, a solution prepared by dissolving 1.00 g of poly-N-vinylcarbazole (weight average molecular weight=63,000) in 80 ml of chloroform was applied to form a film of 110 nm in thickness by spin-coating method (rotation speed=2000 rpm), thereby forming an organic layer (hole-transporting layer 5).

Next, a solution prepared by dissolving 0.050 g of the fluorene compound represented as exemplified compound No. 1 in 50 ml of toluene was applied to form a film of 120 nm in thickness by spin-coating method (rotation speed=2000 rpm) to thereby form an organic layer (light-emitting layer 3).

EXAMPLE 21 to 23

Devices were prepared and evaluated following the same procedure as in Example 21 with the exception that the compounds shown in Table 4 were used in place of exemplified compound No. 1. The results are shown in Table 4.

Comparative Examples 7 and 8

Devices were prepared and evaluated following the same procedure as in Example 21 with the exception that comparative compounds 1 and 2 were used in place of exemplified compound No. 1. The results are shown in Table 4.

TABLE 4

| Example No. | Exemplified Compound No. | Initial Stage | | Durability | | |
|---|---|---|---|---|---|---|
| | | Applied voltage (V) | Luminance (cd/m²) | Current Density (mA/cm²) | Initial Luminance (cd/m²) | Luminance after 100 hours (cd/m²) |
| Example 20 | 1 | 4 | 2200 | 50.0 | 4100 | 3100 |
| Example 21 | 12 | 4 | 2000 | 50.0 | 4000 | 3200 |

TABLE 4-continued

| | | Initial Stage | | Durability | | |
|---|---|---|---|---|---|---|
| Example No. | Exemplified Compound No. | Applied voltage (V) | Luminance (cd/m²) | Current Density (mA/cm²) | Initial Luminance (cd/m²) | Luminance after 100 hours (cd/m²) |
| Example 22 | 16 | 4 | 2100 | 50.0 | 4200 | 3300 |
| Example 23 | 32 | 4 | 2040 | 50.0 | 4090 | 3100 |
| Comparative Example 7 | Comparative Compound 1 | 4 | 750 | 50.0 | 800 | 400 |
| Comparative Example 8 | Comparative Compound 2 | 4 | 620 | 50.0 | 710 | 310 |

What is claimed is:

1. A fluorene compound represented by the following general formula:

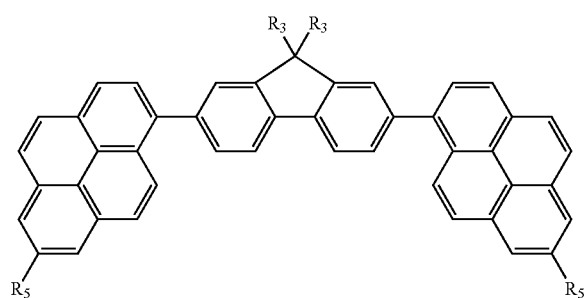

[I-1]

wherein each $R_3$, independently, is a substituted or unsubstituted alkyl group, and each $R_5$, independently, is 1-adamantyl group or 2-adamantyl group.

2. The fluorene compound according to claim 1, which is represented the structural formula:

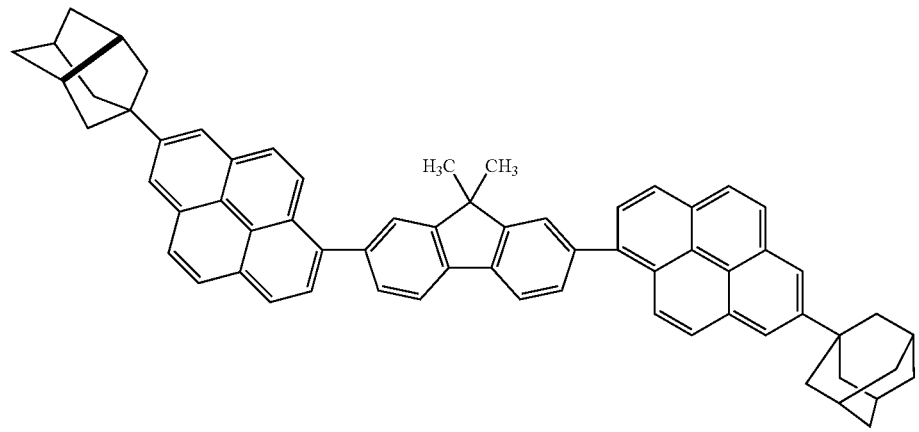

3. An organic light-emitting device comprising a pair of electrodes including an anode and a cathode, and at least one layer comprising an organic compound sandwiched between the pair of electrodes, wherein at least one of the at least one layer comprising the organic compound comprises at least one of the fluorene compounds as set forth in claim 1.

4. The organic light-emitting device according to claim 3, wherein at least an electron-transporting layer or a light-emitting layer of the at least one layer comprising the organic compound comprises at least one of the fluorene compounds.

5. The organic light-emitting device according to claim 3, wherein at least a light-emitting layer of the at least one layer comprising the organic compound comprises (a) the fluorene compound and (b) an arylamine compound represented by the general formula [II]:

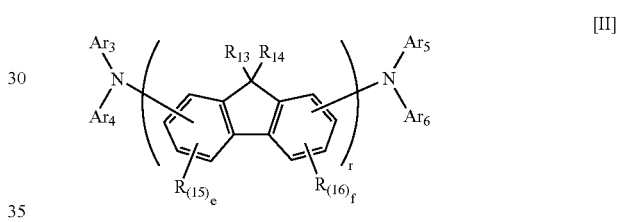

[II]

wherein each $R_{13}$ and $R_{14}$, independently, is a hydrogen atom, a substituted or unsubstituted alkyl group, a substituted or unsubstituted aralkyl group, a substituted or unsubstituted aryl group, or a substituted or unsubstituted heterocyclic group;

each $R_{15}$ and $R_{16}$, independently, is a hydrogen atom, a substituted or unsubstituted alkyl group, a substituted or unsubstituted aralkyl group, a substituted or unsubstituted aryl group, a substituted or unsubstituted heterocyclic group, cyano group, or a halogen atom;

$Ar_3$, $Ar_4$, $Ar_5$, and $Ar_6$ are each independently a substituted or unsubstituted aromatic group, a substituted or unsubstituted heterocyclic group, a substituted or unsubstituted fused polycyclic aromatic group, or a substituted or unsubstituted fused heteropolycyclic group, or $Ar_3$ and $Ar_4$, and $Ar_5$ and $Ar_6$ can respectively be joined to form a ring;

e and f are each independently an integer of 1 to 3; and r is an integer of 1 to 10.

* * * * *